(12) United States Patent
Niemeyer et al.

(10) Patent No.: US 10,675,621 B2
(45) Date of Patent: Jun. 9, 2020

(54) ANLAYSIS SYSTEM FOR TESTING A SAMPLE

(71) Applicant: Boehringer Ingelheim Vetmedica GmbH, Ingelheim am Rhein (DE)

(72) Inventors: Axel Niemeyer, Bielefeld (DE); Hannah Schmolke, Braunschweig (DE)

(73) Assignee: BOEHRINGER INGELHEIM VETMEDICA GMBH, Ingelheim am Rhein (DE)

( * ) Notice: Subject to any disclaimer, the term of this patent is extended or adjusted under 35 U.S.C. 154(b) by 324 days.

(21) Appl. No.: 15/725,336

(22) Filed: Oct. 5, 2017

(65) Prior Publication Data

US 2018/0099278 A1    Apr. 12, 2018

(30) Foreign Application Priority Data

Oct. 7, 2016 (EP) ..................... 16020377

(51) Int. Cl.
| | |
|---|---|
| *B01L 3/00* | (2006.01) |
| *B01J 19/00* | (2006.01) |
| *C12Q 1/6825* | (2018.01) |
| *G01N 33/483* | (2006.01) |
| *F04B 19/00* | (2006.01) |
| *F16K 99/00* | (2006.01) |

(52) U.S. Cl.
CPC ..... *B01L 3/502715* (2013.01); *B01J 19/0093* (2013.01); *B01L 3/5027* (2013.01); *C12Q 1/6825* (2013.01); *F04B 19/006* (2013.01); *G01N 33/483* (2013.01); *B01J 2219/00333* (2013.01); *B01L 2300/0627* (2013.01); *B01L 2300/0636* (2013.01); *B01L 2300/0645* (2013.01); *B01L 2300/0816* (2013.01); *B01L 2300/0819* (2013.01); *B01L 2300/123* (2013.01); *B01L 2400/0487* (2013.01); *F16K 2099/0084* (2013.01)

(58) Field of Classification Search
None
See application file for complete search history.

(56) References Cited

U.S. PATENT DOCUMENTS

| | | | |
|---|---|---|---|
| 5,096,669 | A | 3/1992 | Lauks et al. |
| 7,838,261 | B2 | 11/2010 | Gumbrecht et al. |
| 7,914,655 | B2 | 3/2011 | Frey et al. |
| 8,039,269 | B2 | 10/2011 | Maerkl et al. |
| 8,633,013 | B2 | 1/2014 | Kaiser et al. |
| 9,110,044 | B2 | 8/2015 | Gumbrecht et al. |
| 2015/0184235 | A1 | 7/2015 | Reda et al. |

FOREIGN PATENT DOCUMENTS

| | | |
|---|---|---|
| DE | 10 2014 200 483 A1 | 7/2015 |
| WO | 2005/108604 A2 | 11/2005 |

*Primary Examiner* — Kathryn Wright
(74) *Attorney, Agent, or Firm* — David S. Safran; Roberts Calderon Safran & Cole, P.C.

(57) ABSTRACT

An analysis system for testing a biological sample wherein a sensor cover can be or is pneumatically lowered onto a sensor apparatus in order to detect an analyte of the sample.

33 Claims, 7 Drawing Sheets

ANALYSIS SYSTEM FOR TESTING A SAMPLE

BACKGROUND OF THE INVENTION

Field of the Invention

The present invention relates to an analysis system, in particular a cartridge, for testing a biological sample, the analysis system comprising a main body having a plurality of channels, and comprising a sensor arrangement for detecting an analyte of the sample.

Preferably, the present invention deals with analysing and testing a sample, in particular from a human or animal, particularly preferably for analytics and diagnostics, for example with regard to the presence of diseases and/or pathogens and/or for determining blood counts, antibodies, hormones, steroids or the like. Therefore, the present invention is in particular within the field of bioanalytics. A food sample, environmental sample or another sample may optionally also be tested, in particular for environmental analytics or food safety and/or for detecting other substances.

Preferably, by means of the present invention, at least one analyte (target analyte) of a sample can be determined, identified or detected. In particular, the sample can be tested for qualitatively or quantitatively determining at least one analyte, for example in order for it to be possible to detect or identify a disease and/or pathogen.

Within the meaning of the present invention, analytes are in particular nucleic-acid sequences, in particular DNA sequences and/or RNA sequences, and/or proteins, in particular antigens and/or antibodies. In particular, by means of the present invention, nucleic-acid sequences can be determined, identified or detected as analytes of a sample, and/or proteins can be determined, identified or detected as analytes of the sample. More particularly preferably, the present invention deals with systems, devices and other apparatuses for carrying out a nucleic-acid assay for detecting a nucleic-acid sequence and/or a protein assay for detecting or identifying a protein.

The present invention deals in particular with what are known as point-of-care systems, i.e. within particular mobile systems, devices and other apparatuses, and deals with methods for carrying out tests on a sample at the sampling site and/or independently or away from a central laboratory or the like. Preferably, point-of-care systems can be operated autonomously or independently of a mains network for supplying electrical power.

Description of Related Art

U.S. Pat. No. 5,096,669 discloses a point-of-care system for testing a biological sample, in particular a blood sample. The system comprises a single-use cartridge and an analysis device. Once the sample has been received, the cartridge is inserted into the analysis device in order to carry out the test. The cartridge comprises a microfluidic system and a sensor apparatus comprising electrodes, which apparatus is calibrated by means of a calibration liquid and is then used to test the sample.

Furthermore, WO 2006/125767 A1 discloses a point-of-care system for integrated and automated DNA or protein analysis, comprising a single-use cartridge and an analysis device for fully automatically processing and evaluating molecular-diagnostic analyses using the single-use cartridge. The cartridge is designed to receive a sample, in particular blood, and in particular allows cell disruption, PCR and detection of PCR amplification products, which are bonded to capture molecules and provided with a label enzyme, in order for it to be possible to detect bonded PCR amplification products or nucleic-acid sequences as target analytes in what is known as a redox cycling process.

DE 100 58 394 C1 discloses a method for testing a sample using a reaction array comprising at least two reaction compartments for receiving substances that react with one another, the reaction compartments being interconnected by means of a supply space. In order to measure the substances, an exchange of substances and thus chemical crosstalk between the individual reaction compartments is prevented by lowering a sensor cover. In this way, the detection sensitivity of the method is increased.

DE 10 2014 200 483 A1 discloses a microfluidic chip for analysing a sample. A fluid can be displaced from a reaction chamber by lowering a flexible membrane in the chamber. The membrane separates the reaction chamber from an air chamber and is lowered or pressed down by applying pressure to the membrane via the air chamber. The membrane has a given, constant thickness and, thus does not allow optimized operation characteristics.

WO 2007/089587 A2 discloses a microfluidic device for detection and analysis of interactions between molecules. Chambers in which molecules can be trapped and analyzed are formed by flexible membranes adhered to a plane glass substrate. The sides of the membranes facing the substrate have concave recesses so that the chambers are formed between the concave recesses and the plane substrate. Molecules to be analyzed can be mechanically trapped by pneumatically pressing down the membrane. The form of the membranes does not allow optimized operation.

WO 2008/135564 A2 discloses a microfluidic device for performing assays. Channels for a sample are defined between a rigid substrate and a deformable substrate being made of flexible material, both substrates being generally planar. A sample can be moved within the microfluidic device by pressing down the deformable substrate with a roller. The substrates are shown to have at least essentially constant thicknesses. It is not explained how the substrates are connected. The form of the substrate does not allow optimized operation.

SUMMARY OF THE INVENTION

The problem addressed by the present invention is to provide an improved analysis system and an improved method for testing a sample, a simple, compact, stable and/or cost-effective design of the analysis system and/or efficient, rapid, reliable and/or precise testing of the sample and/or reliable sealing of individual positions or fields of a sensor array being made possible or facilitated.

The above problem is solved by an analysis system as described herein.

The proposed analysis system for testing an in particular biological sample preferably comprises a sensor arrangement for identifying or detecting an analyte of the sample, the sensor arrangement preferably comprising a sensor apparatus having capture molecules and a sensor cover that is flexible at least in part for covering the sensor apparatus.

The sensor apparatus is preferably designed to carry out a protein assay and/or a nucleic-acid assay. In particular, the sensor apparatus comprises capture proteins as capture molecules for detecting or identifying a target protein and/or comprises capture nucleic-acid sequences as capture molecules for detecting or identifying a target nucleic-acid sequence, in particular in order to bond corresponding target proteins to the capture proteins and to bond corresponding target nucleic-acid sequences to the capture nucleic-acid sequences.

The sensor apparatus is preferably designed for electrochemically detecting analytes bonded to the capture molecules. The sensor apparatus preferably comprises a sensor array comprising a plurality of sensor fields and/or electrodes.

One aspect of the present invention is that the sensor cover can be actuated and/or lowered onto the sensor apparatus preferably pneumatically, in particular by means of a working medium such as gas, in particular in order to seal and/or fluidically separate individual positions and/or sensor fields of the sensor apparatus from one another.

The analysis system is in particular portable, mobile and/or is a point-of-care system and/or can be used in particular at the sampling site and/or away from a central laboratory.

The analysis system preferably comprises an analysis device and a cartridge for testing the sample, the cartridge preferably being designed for receiving the sample and the analysis device preferably being designed for receiving the cartridge.

Particularly preferably, the analysis device is designed to receive the cartridge or to connect said cartridge electrically, thermally and/or pneumatically.

Particularly preferably, the analysis device is fluidically, in particular pneumatically, connected or connectable to the cartridge and/or is designed to supply the cartridge with a working medium, in particular gas, in order to actuate the sensor cover and/or to lower said cover onto the sensor apparatus.

The pneumatic actuation of the sensor cover allows particularly reliable and rapid actuation of the sensor cover. Furthermore, a construction of this kind allows or facilitates a particularly simple and compact design of the analysis system and/or of the cartridge. In particular, no mechanical and/or movable components are required for actuating the sensor cover.

The sensor cover preferably comprises a cover part, a side part and a connecting part that is flexible and/or extensible at least in part, the cover part preferably being able to be lowered onto the sensor apparatus and/or sensor fields, and/or being connected to the side part by means of the connecting part. Particularly preferably, the sensor cover is formed in one piece or the sensor cover forms a unit. In particular, the sensor cover is made of and/or injection-moulded from plastics material, particularly preferably from an elastomer.

According to another aspect of the present invention, which can also be implemented independently, when it is unactuated and/or moved away from the sensor apparatus, the sensor cover has a raised portion in the centre on a side remote from the sensor apparatus and is at least substantially flat or planar on a side facing the sensor apparatus.

Particularly preferably, the sensor cover, in particular the cover part, is reinforced.

A construction of this kind makes it possible to lower the sensor cover and/or the cover part onto the sensor apparatus at least substantially evenly and/or in an uncurved manner and/or with a planar flat side, and/or to close and/or fluidically separate all the sensor fields of the sensor apparatus from one another at least substantially simultaneously. In particular, the centre of the sensor cover and/or the cover part is not or at least substantially not curved or bent during actuation.

The central raised portion and/or reinforcement of the sensor cover in particular ensures that the sensor fields in the edge region of the sensor apparatus are also closed and/or sealed by the sensor cover and/or the cover part.

According to another aspect of the present invention, which can also be implemented independently, in the edge region, the sensor apparatus is pressed against the sensor cover and/or the side part and/or is sealingly mounted on the sensor cover and/or the side part in the edge region.

The side part holds or surrounds the cover part, preferably peripherally and/or in a frame-like or collar-like manner. In particular, the sensor cover is held and/or clamped in the analysis system and/or in the cartridge at the edge and/or by the side part.

Particularly preferably, the sensor cover and/or the side part forms a seal for the sensor apparatus. In particular, the sensor cover is designed and/or installed so as to close the sensor fields and to seal the sensor apparatus at the edge. This allows or facilitates a particularly compact design of the analysis system and/or of the cartridge.

The cartridge preferably comprises an in particular at least substantially planar, flat, plate-shaped and/or card-like main body, the sensor cover and the sensor apparatus preferably being received in the main body. Particularly preferably, the sensor apparatus is held by the main body and/or pressed against the sensor cover in a form-fit or interlocking manner in the edge region, in particular such that the sensor apparatus is sealingly mounted on the sensor cover and/or on the side part of the sensor cover in the edge region.

According to another aspect of the present invention, which can also be implemented independently, the sensor arrangement comprises a sensor compartment delimited or defined by the sensor apparatus and the sensor cover, an inlet into the sensor compartment and an outlet out of the sensor compartment, the inlet and/or outlet extending through the sensor cover, in particular the side part, at least in portions. In particular, the inlet and/or the outlet is/are sealed by the sensor cover and/or the side part. This allows or facilitates a particularly compact design and reliable sealing of the sensor compartment.

In the proposed method for testing an in particular biological sample, analytes of the sample are bonded to capture molecules of a sensor apparatus, and the bonded analytes are detected, preferably electrochemically or by means of redox cycling, a sensor cover that is preferably flexible at least in part being lowered onto the sensor apparatus for the detection, in particular in order to seal and/or fluidically separate sensor fields of the sensor apparatus from one another. The sensor cover is preferably actuated pneumatically and/or by means of pressurised air. This results in corresponding advantages.

Preferably, in the method, the sample is placed into a cartridge, and the cartridge containing the sample is received by an analysis device at least in part. The analysis device is (then) preferably pneumatically connected to the cartridge, in particular to a sensor arrangement of the cartridge, in order to actuate the sensor cover and/or to lower said cover onto the sensor apparatus in order to detect the bonded analytes.

Preferably, a working medium, in particular a gas, is pressurised by the analysis device and is fed to the cartridge from the outside. In particular, the pressure is generated outside the cartridge and/or by means of the analysis device. Advantageously, the complexity of the cartridge is thus reduced.

The term "analysis device" is preferably understood to mean an instrument which is in particular mobile and/or can be used on site, and/or which is designed to chemically, biologically and/or physically test and/or analyse a sample or a component thereof, preferably in and/or by means of a cartridge. In particular, the analysis device controls the pretreatment and/or testing of the sample in the cartridge.

The term "cartridge" is preferably understood to mean a structural apparatus or unit designed to receive, to store, to physically, chemically and/or biologically treat and/or prepare and/or to measure a sample, preferably in order to make it possible to detect, identify or determine at least one analyte, in particular a protein and/or a nucleic-acid sequence, of the sample.

A cartridge within the meaning of the present invention preferably comprises a fluid system having a plurality of channels, cavities and/or valves for controlling the flow through the channels and/or cavities.

In particular, within the meaning of the present invention, a cartridge is designed to be at least substantially planar and/or card-like, in particular is designed as a (micro)fluidic card and/or is designed as a main body or container that can preferably be closed and/or said cartridge can be inserted and/or plugged into a proposed analysis device when it contains the sample.

The above-mentioned aspects and features of the present invention and the aspects and features of the present invention that will become apparent from the claims and the following description can in principle be implemented independently from one another, but also in any combination or order.

Other aspects, advantages, features and properties of the present invention will become apparent from the claims and the following description of a preferred embodiment with reference to the drawings, in which:

DETAILED DESCRIPTION OF THE INVENTION

In the Figures, which are only schematic and sometimes not to scale, the same reference signs are used for the same or similar parts and components, corresponding or comparable properties and advantages being achieved even if these are not repeatedly described.

Figure 1:
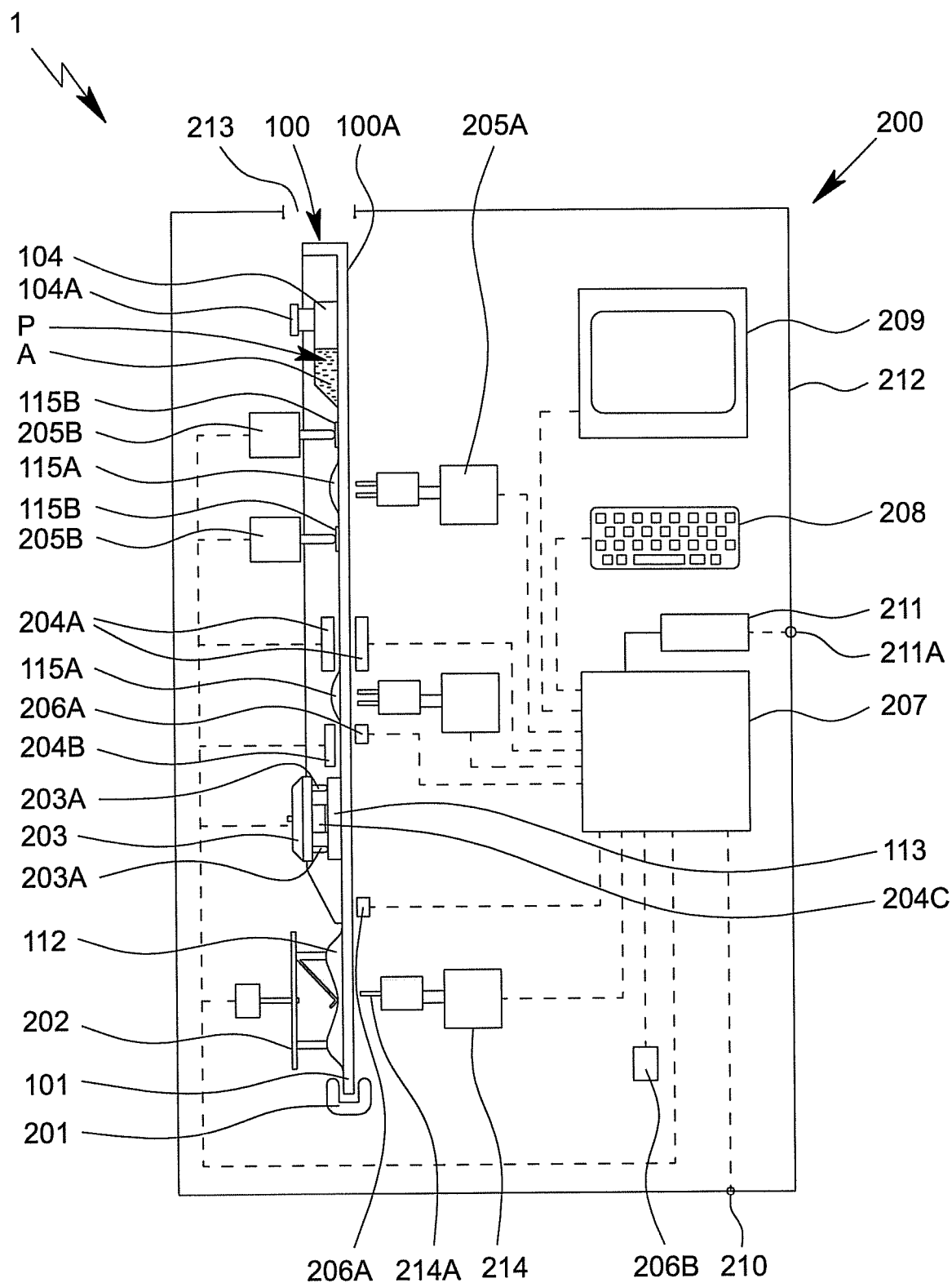
FIG. 1 is a schematic view of a proposed analysis system and/or analysis device comprising a proposed cartridge received therein.

FIG. 1 is a highly schematic view of a proposed analysis system 1 and analysis device 200 for testing an in particular biological sample P, preferably by means of or in an apparatus or cartridge 100.

Figure 2:
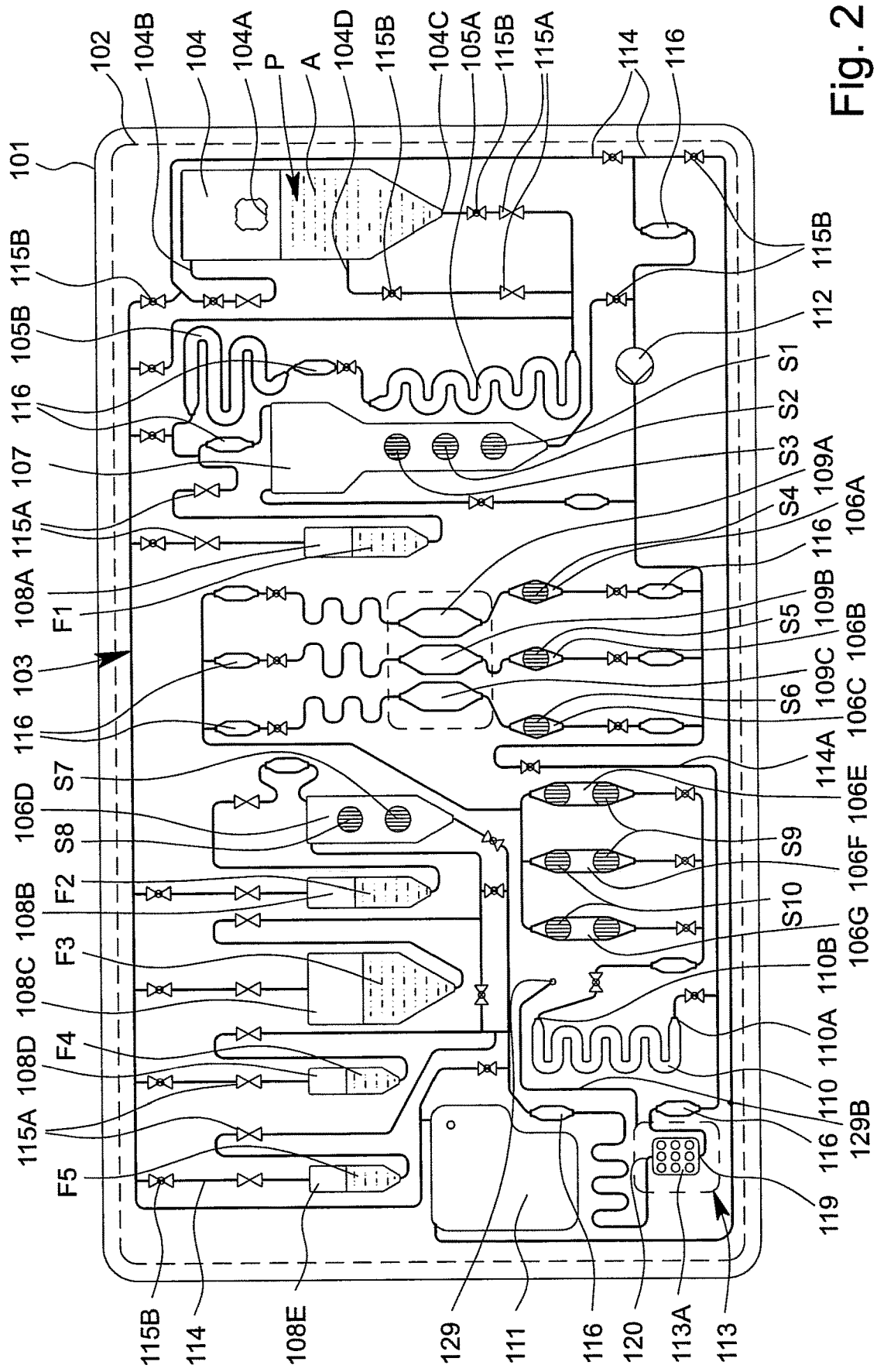
FIG. 2 is a schematic view of the cartridge.

FIG. 2 is a schematic view of a preferred embodiment of the proposed apparatus or cartridge 100 for testing the sample P. The apparatus or cartridge 100 in particular forms a handheld unit, and in the following is merely referred to as a cartridge.

The term "sample" is preferably understood to mean the sample material to be tested, which is in particular taken from a human or animal. In particular, within the meaning of the present invention, a sample is a fluid, such as saliva, blood, urine or another liquid, preferably from a human or animal, or a component thereof. Within the meaning of the present invention, a sample may be pretreated or prepared if necessary, or may come directly from a human or animal or the like, for example. A food sample, environmental sample or another sample may optionally also be tested, in particular for environmental analytics, food safety and/or for detecting other substances, preferably natural substances, but also biological or chemical warfare agents, poisons or the like.

Preferably, the analysis system 1 or analysis device 200 controls the testing of the sample P in particular in or on the cartridge 10Q and/or is used to evaluate the testing or the collection, processing and/or storage of measured values from the test.

By means of the proposed analysis system 1, analysis device 200 and/or the cartridge 100 and/or using the proposed method for testing the sample P, preferably an analyte A of the sample P, in particular a (certain) nucleic-acid sequence and/or a (certain) protein, or particularly preferably a plurality of analytes A of the sample P, can be determined, identified or detected. Said analytes are in particular detected and/or measured not only qualitatively, but particularly preferably also quantitatively.

Therefore, the sample P can in particular be tested for qualitatively or quantitatively determining at least one analyte A, for example in order for it to be possible to detect a disease and/or pathogen or to determine other values, which are important for diagnostics, for example.

Particularly preferably, a molecular-biological test is made possible by means of the analysis system 1 and/or analysis device 200 and/or by means of the cartridge 10Q.

Particularly preferably, a nucleic-acid assay for detecting or identifying a nucleic-acid sequence, in particular a DNA sequence and/or RNA sequence, and/or a protein assay for detecting or identifying a protein, in particular an antigen and/or antibody, are made possible or are carried out.

Preferably, the sample P or individual components of the sample P or analyte A can be amplified if necessary, in particular by means of PCR, and tested, identified or detected in the analysis system 1, analysis device 200 and/or in the cartridge 100, and/or for the purpose of carrying out the nucleic-acid assay. Preferably, amplification products of the analyte A or analytes A are thus produced.

In the following, further details are first given on a preferred construction of the cartridge 100, with features of the cartridge 100 preferably also directly representing features of the analysis system 1, in particular even without any further explicit explanation.

The cartridge 100 is preferably at least substantially planar, flat and/or plate-shaped and/or card-like.

The cartridge 100 preferably comprises an in particular at least substantially planar, flat, plate-shaped and/or card-like main body or support 101, the main body or support 101 in particular being made of and/or injection-moulded from plastics material, particularly preferably polypropylene.

The cartridge 100 preferably comprises at least one film or cover 102 for covering the main body 101 and/or cavities and/or channels formed therein at least in part, in particular on the front, and/or for forming valves or the like, as shown by dashed lines in FIG. 2.

The analysis system 1 or cartridge 100 or the main body 101 thereof, in particular together with the cover 102, preferably forms and/or comprises a fluidic system 103, referred to in the following as the fluid system 103.

The cartridge 100, the main body 101 and/or the fluid system 103 are preferably at least substantially vertically oriented in the operating position and/or during the test, in particular in the analysis device 200, as shown schematically in FIG. 1. In particular, the main plane or surface extension of the cartridge 100 thus extends at least substantially vertically in the operating position.

The cartridge 100 and/or the fluid system 103 preferably comprises a plurality of cavities, in particular at least one receiving cavity 104, at least one metering cavity 105, at least one intermediate cavity 106, at least one mixing cavity 107, at least one storage cavity 108, at least one reaction cavity 109, at least one intermediate temperature-control cavity 110 and/or at least one collection cavity 111, as shown in FIG. 1 and FIG. 2.

The cartridge 100 and/or the fluid system 103 also preferably comprises at least one pump apparatus 112 and/or at least one sensor arrangement or sensor apparatus 113.

Some, most or all of the cavities are preferably formed by chambers and/or channels or other depressions in the cartridge 100 and/or the main body 101, and particularly preferably are covered or closed by the cover 102. However, other structural solutions are also possible.

In the example shown, the cartridge 100 or the fluid system 103 preferably comprises two metering cavities 105A and 105B, a plurality of intermediate cavities 106A to 106G, a plurality of storage cavities 108A to 108E and/or a plurality of reaction cavities 109, which can preferably be loaded separately from one another, in particular a first reaction cavity 109A, a second reaction cavity 109B and an optional third reaction cavity 109C, as can be seen in FIG. 2.

The reaction cavity/cavities 109 is/are used in particular to carry out an amplification reaction, in particular PCR, or several, preferably different, amplification reactions, in particular PCRs. It is preferable to carry out several, preferably different, PCRs, i.e. PCRs having different primer combinations or primer pairs, in parallel and/or independently and/or in different reaction cavities 109.

To carry out the nucleic-acid assay, preferably nucleic-acid sequences, as analytes A of the sample P, are amplified in the reaction cavity/cavities 109 by means of an amplification reaction, in particular in order to produce amplification products for the subsequent detection in the sensor arrangement or sensor apparatus 113.

Within the meaning of the present invention, amplification reactions are in particular molecular-biological reactions in which an analyte A, in particular a nucleic-acid sequence, is amplified/copied and/or in which amplification products, in particular nucleic-acid products, of an analyte A are produced. Particularly preferably, PCRs are amplification reactions within the meaning of the present invention.

"PCR" stands for polymerase chain reaction and is a molecular-biological method by means of which certain analytes A, in particular portions of RNA or RNA sequences or DNA or DNA sequences, of a sample P are amplified, preferably in several cycles, using polymerases or enzymes, in particular in order to then test and/or detect the amplification products or nucleic-acid products. If RNA is intended to be tested and/or amplified, before the PCR is carried out, a cDNA is produced starting from the RNA, in particular using reverse transcriptase. The cDNA is used as a template for the subsequent PCR.

Preferably, during a PCR, a sample P is first denatured by the addition of heat in order to separate the strands of DNA or cDNA. Preferably, primers or nucleotides are then deposited on the separated single strands of DNA or cDNA, and a desired DNA or cDNA sequence is replicated by means of polymerase and/or the missing strand is replaced by means of polymerase. This process is preferably repeated in a plurality of cycles until the desired quantity of the DNA or cDNA sequence is available.

For the PCR, marker primers are preferably used, i.e. primers which (additionally) produce a marker or a label, in particular biotin, on the amplified analyte A or amplification product. This allows or facilitates detection. Preferably, the primers used are biotinylated and/or comprise or form in particular covalently bonded biotin as the label.

The amplification products and/or other portions of the sample P produced in the one or more reaction cavities 109 can be conducted or fed to the connected sensor arrangement or sensor apparatus 113, in particular by means of the pump apparatus 112.

The sensor apparatus 113 is used in particular for detecting, particularly preferably qualitatively and/or quantitatively determining, the analyte A or analytes A of the sample P, in this case particularly preferably the nucleic-acid sequences and/or proteins as the analytes A. Alternatively or additionally, however, other values may also be collected or determined.

As already explained at the outset, in particular nucleic-acid sequences, preferably DNA sequences and/or RNA sequences, and/or proteins, in particular antigens and/or antibodies, are preferably qualitatively and/or quantitatively determined as analytes A of the sample P. In the following, however, a distinction is not made between nucleic-acid sequences and proteins, or between the nucleic-acid assay for detecting nucleic-acid sequences and the protein assay for detecting proteins.

In particular, the pump apparatus 112 comprises or forms a tube-like or bead-like raised portion, in particular by means of the film or cover 102, particularly preferably on the back 100B of the cartridge 100, as shown schematically in FIG. 1.

The cartridge 100, the main body 101 and/or the fluid system 103 preferably comprise a plurality of channels 114 and/or valves 115, as shown in FIG. 2.

By means of the channels 114 and/or valves 115, the cavities 104 to 111, the pump apparatus 112 and/or the sensor arrangement and/or sensor apparatus 113 can be temporarily and/or permanently fluidically interconnected and/or fluidically separated from one another, as required and/or optionally, or selectively, in particular such that they are controlled by the analysis system 1 or the analysis device 200.

The cavities 104 to 111 are preferably each fluidically linked or interconnected by a plurality of channels 114. Particularly preferably, each cavity is linked or connected by at least two associated channels 114, in order to make it possible for fluid to fill, flow through and/or drain from the respective cavities as required.

The fluid transport or the fluid system 103 is preferably not based on capillary forces, or is not exclusively based on said forces, but in particular is essentially based on the effects of gravity and/or pumping forces and/or compressive forces and/or suction forces that arise, which are particularly preferably generated by the pump or pump apparatus 112. In this case, the flows of fluid or the fluid transport and the metering are controlled by accordingly opening and closing the valves 115 and/or by accordingly operating the pump or pump apparatus 112, in particular by means of a pump drive 202 of the analysis device 200.

Preferably, each of the cavities 104 to 110 has an inlet at the top and an outlet at the bottom in the operating position. Therefore, if required, only liquid from the respective cavities can be removed via the outlet.

In the operating position, the liquids from the respective cavities are preferably removed, in particular drawn out, via the outlet that is at the bottom in each case, it preferably being possible for gas or air to flow and/or be pumped into the respective cavities via the inlet that is in particular at the top. In particular, relevant vacuums in the cavities can thus be prevented or at least minimised when conveying the liquids.

In particular, the cavities, particularly preferably the storage cavity/cavities 108, the mixing cavity 107 and/or the receiving cavity 104, are each dimensioned and/or oriented in the normal operating position such that, when said cavities are filled with liquid, bubbles of gas or air that may potentially form rise upwards in the operating position, such that the liquid collects above the outlet without bubbles. However, other solutions are also possible here.

The receiving cavity 104 preferably comprises a connection 104A for introducing the sample P. In particular, the sample P may for example be introduced into the receiving cavity 104 and/or cartridge 100 via the connection 104A by means of a pipette, syringe or other instrument.

The receiving cavity 104 preferably comprises an inlet 104B, an outlet 104C and an optional intermediate connection 104D, it preferably being possible for the sample P or a portion thereof to be removed and/or conveyed further via the outlet 104C and/or the optional intermediate connection 104D. Gas, air or another fluid can flow in and/or be pumped in via the inlet 104B, as already explained.

Preferably, the sample P or a portion thereof can be removed, optionally and/or depending on the assay to be carried out, via the outlet 104C or the optional intermediate connection 104D of the receiving cavity 104. In particular, a supernatant of the sample P, such as blood plasma or blood serum, can be conducted away or removed via the optional intermediate connection 104D, in particular for carrying out the protein assay.

Preferably, at least one valve 115 is assigned to each cavity, the pump apparatus 112 and/or the sensor apparatus 113 and/or is arranged upstream of the respective inlets and/or downstream of the respective outlets.

Preferably, the cavities 104 to 111 or sequences of cavities 104 to 111, through which fluid flows in series or in succession for example, can be selectively released and/or fluid can selectively flow therethrough by the assigned valves 115 being actuated, and/or said cavities can be fluidically connected to the fluid system 103 and/or to other cavities.

In particular, the valves 115 are formed by the main body 101 and the film or cover 102 and/or are formed in another manner, for example by additional layers, depressions or the like.

Particularly preferably, one or more valves 115A are provided which are preferably tightly closed initially or when in storage, particularly preferably in order to seal liquids or liquid reagents F, located in the storage cavities 108, and/or the fluid system 103 from the open receiving cavity 104 in a storage-stable manner.

Preferably, an initially closed valve 115A is arranged upstream and downstream of each storage cavity 108. Said valves are preferably only opened, in particular automatically, when the cartridge 100 is actually being used and/or while inserting the cartridge 100 into the analysis device 200 and/or for carrying out the assay.

A plurality of valves 115A, in particular three valves in this case, are preferably assigned to the receiving cavity 104, in particular if the intermediate connection 104D is provided in addition to the inlet 104B and the outlet 104C. Depending on the use, in addition to the valve 115A on the inlet 104B, then preferably only the valve 115A either at the outlet 104C or at the intermediate connection 104D is opened.

The valves 115A assigned to the receiving cavity 104 seal the fluid system 103 and/or the cartridge 100 in particular fluidically and/or in a gas-tight manner until the sample P is inserted and the receiving cavity 104 or a connection 104A of the receiving cavity 104 is closed.

As an alternative or in addition to the valves 115A (which are initially closed), one or more valves 115B are preferably provided which are not closed in a storage-stable manner and/or which are open initially and/or which can be closed by actuation. These valves are used in particular to control the flows of fluid during the test.

The cartridge 100 is preferably designed as a microfluidic card and/or the fluid system 103 is preferably designed as a microfluidic system. In the present invention, the term "microfluidic" is preferably understood to mean that the respective volumes of individual cavities, some of the cavities or all of the cavities 104 to 111 and/or channels 114 are, separately or cumulatively, less than 5 ml or 2 ml, particularly preferably less than 1 ml or 800 µl, in particular less than 600 µl or 300 µl, more particularly preferably less than 200 µl or 100 µl.

Particularly preferably, a sample P having a maximum volume of 5 ml, 2 ml or 1 ml can be introduced into the cartridge 100 and/or the fluid system 103, in particular the receiving cavity 104.

Reagents and liquids which are preferably introduced or provided before the test in liquid form as liquids or liquid reagents F and/or in dry form as dry reagents S are required for testing the sample P, as shown in the schematic view according to FIG. 2 by reference signs F1 to F5 and S1 to S10.

Furthermore, other liquids F, in particular in the form of a wash buffer, solvent for dry reagents S and/or a substrate SU, for example in order to form detection molecules and/or a redox system, are also preferably required for the test, the detection process and/or for other purposes, and are in particular provided in the cartridge 100, i.e. are likewise introduced before use, in particular before delivery. At some points in the following, a distinction is not made between liquid reagents and other liquids, and therefore the respective explanations are accordingly also mutually applicable.

The analysis system 1 and/or the cartridge 100 preferably contains all the reagents and liquids required for pretreating the sample P and/or for carrying out the test or assay, in particular for carrying out one or more amplification reactions or PCRs, and therefore, particularly preferably, it is only necessary to receive the optionally pretreated sample P.

The cartridge 100 and/or the fluid system 103 preferably comprises a bypass 114A that can optionally be used, in order for it to be possible, if necessary, to conduct or convey the sample P or components thereof past the reaction cavities 109 and/or, by bypassing the optional intermediate temperature-control cavity 110, also directly to the sensor apparatus 113.

The cartridge 100, the fluid system 103 and/or the channels 114 preferably comprise sensor portions 116 or other apparatuses for detecting liquid fronts and/or flows of fluid.

It is noted that various components, such as the channels 114, the valves 115, in particular the valves 115A that are initially closed and the valves 115B that are initially open, and the sensor portions 116 in FIG. 2 are, for reasons of clarity, only labelled in some cases, but the same symbols are used in FIG. 2 for each of these components.

The collection cavity 111 is preferably used for receiving excess or used reagents and liquids and volumes of the sample, and/or for providing gas or air in order to empty individual cavities and/or channels.

In particular, the collection cavity 111 can optionally be connected to individual cavities and channels or other apparatuses fluidically in order to remove reagents and liquids from said cavities, channels or other apparatuses and/or to replace said reagents and liquids with gas or air. The collection cavity 111 is preferably given appropriate large dimensions.

Once the sample P has been introduced into the receiving cavity 104 and the connection 104A has been closed, the cartridge 100 can be inserted into and/or received in the proposed analysis device 200 in order to test the sample P, as shown in FIG. 1. Alternatively, the sample P could also be fed in later.

FIG. 1 shows the analysis system 1 in a ready-to-use state for carrying out a test or assay on the sample P received in the cartridge 100. In this state, the cartridge 100 is therefore linked to, received by and/or inserted into the analysis device 200.

In the following, some features and aspects of the analysis device 200 are first explained in greater detail, in particular on the basis of FIG. 1. The features and aspects relating to said device are preferably also directly features and aspects of the proposed analysis system 1, in particular even without any further explicit explanation.

The analysis system 1 or analysis device 200 preferably comprises a mount or receptacle 201 for mounting and/or receiving the cartridge 100.

Preferably, the cartridge 100 is fluidically, in particular hydraulically, separated or isolated from the analysis device 200. In particular, the cartridge 100 forms a preferably independent and in particular closed or sealed fluidic and/or hydraulic system 103 for the sample P and the reagents and other liquids. In this way, the analysis device 200 does not come into direct contact with the sample P and can in particular be reused for another test without being disinfected and/or cleaned first.

It is however provided that the analysis device 200 can be connected or coupled mechanically, electrically, thermally and/or pneumatically to the cartridge 100.

In particular, the analysis device 200 is designed to have a mechanical effect or act mechanically on the cartridge 100, in particular for actuating the pump apparatus 112 and/or the valves 115, and/or to have a thermal effect or act thermally on the cartridge 100, in particular for temperature-controlling the reaction cavity/cavities 109 and/or the intermediate temperature-control cavity 110.

In addition, the analysis device 200 can preferably be pneumatically connected to the cartridge 100, in particular in order to actuate individual apparatuses, and/or can be electrically connected to the cartridge 100, in particular in order to collect and/or transmit measured values, for example from the sensor apparatus 113 and/or sensor portions 116.

The analysis system 1 or analysis device 200 preferably comprises a pump drive 202, the pump drive 202 in particular being designed for mechanically actuating the pump apparatus 112.

Preferably, a head of the pump drive 202 can be rotated in order to rotationally axially depress the preferably bead-like raised portion of the pump apparatus 112. Particularly preferably, the pump drive 202 and pump apparatus 112 together form a pump, in particular in the manner of a hose pump or peristaltic pump and/or a metering pump, for the fluid system 103 and/or the cartridge 100.

Particularly preferably, the pump is constructed as described in DE 10 2011 015 184 B4. However, other structural solutions are also possible.

Preferably, the capacity and/or discharge rate of the pump can be controlled and/or the conveying direction of the pump and/or pump drive 202 can be switched. Preferably, fluid can thus be pumped forwards or backwards as desired.

The analysis system 1 or analysis device 200 preferably comprises a connection apparatus 203 for in particular electrically and/or thermally connecting the cartridge 100 and/or the sensor arrangement or sensor apparatus 113.

As shown in FIG. 1, the connection apparatus 203 preferably comprises a plurality of electrical contact elements 203A, the cartridge 100, in particular the sensor arrangement or sensor apparatus 113, preferably being electrically connected or connectable to the analysis device 200 by the contact elements 203A.

The analysis system 1 or analysis device 200 preferably comprises one or more temperature-control apparatuses 204 for temperature-controlling the cartridge 100 and/or having a thermal effect on the cartridge 100, in particular for heating and/or cooling, the temperature-control apparatus(es) 204 (each) preferably comprising or being formed by a heating resistor or a Peltier element.

Individual temperature-control apparatuses 204, some of these apparatuses or all of these apparatuses can preferably be positioned against the cartridge 100, the main body 101, the cover 102, the sensor arrangement, sensor apparatus 113 and/or individual cavities and/or can be thermally coupled thereto and/or can be integrated therein and/or in particular can be operated or controlled electrically by the analysis device 200. In the example shown, in particular the temperature-control apparatuses 204A, 204B and/or 204C are provided.

Preferably, the temperature-control apparatus 204A, referred to in the following as the reaction temperature-control apparatus 204A, is assigned to the reaction cavity 109 or to a plurality of reaction cavities 109, in particular in order for it to be possible to carry out one or more amplification reactions therein.

The reaction cavities 109 are preferably temperature-controlled simultaneously and/or uniformly, in particular by means of one common reaction temperature-control apparatus 204A or two reaction temperature-control apparatuses 204A.

More particularly preferably, the reaction cavity/cavities 109 can be temperature-controlled from two different sides and/or by means of two or the reaction temperature-control apparatuses 204A that are preferably arranged on opposite sides.

Alternatively, each reaction cavity 109 can be temperature-controlled independently and/or individually.

The temperature-control apparatus 204B, referred to in the following as the intermediate temperature-control apparatus 204B, is preferably assigned to the intermediate temperature-control cavity 110 and/or is designed to (actively) temperature-control and/or heat the intermediate temperature-control cavity 110 or a fluid located therein, in particular the amplification products, preferably to a preheat temperature.

The intermediate temperature-control cavity 110 and/or intermediate temperature-control apparatus 204B is preferably arranged upstream of or (immediately) before the sensor arrangement or sensor apparatus 113, in particular in order for it to be possible to temperature-control and/or preheat, in a desired manner, fluids to be fed to the sensor arrangement or sensor apparatus 113, in particular analytes A and/or amplification products, particularly preferably immediately before said fluids are fed.

Particularly preferably, the intermediate temperature-control cavity 110 and/or intermediate temperature-control apparatus 204B is designed or intended to denature the sample P or analytes A and/or the amplification products produced, and/or to divide any double-stranded analytes A or amplification products into single strands and/or to counteract premature bonding and/or hybridising of the amplification products, in particular by the addition of heat.

Preferably, the analysis system 1, analysis device 200 and/or the cartridge 100 and/or one or each temperature-control apparatus 204 comprise/comprises a temperature detector and/or temperature sensor (not shown), in particular in order to make it possible to control and/or regulate temperature.

One or more temperature sensors may for example be assigned to the sensor portions 116 and/or to individual channel portions or cavities, i.e. may be thermally coupled thereto.

The temperature-control apparatus 204C, referred to in the following as the sensor temperature-control apparatus 204C, is in particular assigned to the sensor apparatus 113 and/or is designed to (actively) temperature-control and/or heat fluids located in or on the sensor arrangement or sensor apparatus 113, in particular analytes A and/or amplification products, reagents or the like, in a desired manner, preferably to a hybridisation temperature.

The sensor temperature-control apparatus 204C is preferably planar and/or has a contact surface which is preferably rectangular and/or corresponds to the dimensions of the sensor arrangement or sensor apparatus 113, the contact surface allowing for heat transfer between the sensor temperature-control apparatus 204C and the sensor apparatus 113.

Preferably, the analysis device 200 comprises the sensor temperature-control apparatus 204C. However, other structural solutions are also possible in which the sensor temperature-control apparatus 204C is integrated in the cartridge 100, in particular the sensor arrangement or sensor apparatus 113.

Particularly preferably, the connection apparatus 203 comprises the sensor temperature-control apparatus 204C, and/or the connection apparatus 203 together with the sensor temperature-control apparatus 204C can be linked to, in particular pressed against, the cartridge 100, in particular the sensor arrangement or sensor apparatus 113.

More particularly preferably, the connection apparatus 203 and the sensor temperature-control apparatus 204C (together) can be moved toward and/or relative to the cartridge 100, in particular the sensor arrangement or sensor apparatus 113, and/or can be positioned against said cartridge, preferably in order to both electrically and thermally couple the analysis device 200 to the cartridge 100, in particular the sensor arrangement or sensor apparatus 113 or the support 113D thereof.

Preferably, the sensor temperature-control apparatus 204C is arranged centrally on the connection apparatus 203 or a support thereof and/or is arranged between the contact elements 203A.

In particular, the contact elements 203A are arranged in an edge region of the connection apparatus 203 or a support thereof or are arranged around the sensor temperature-control apparatus 204C, preferably such that the connection apparatus 203 is connected or connectable to the sensor apparatus 113 thermally in the centre and electrically on the outside or in the edge region. However, other solutions are also possible here.

The analysis system 1 or analysis device 200 preferably comprises one or more actuators 205 for actuating the valves 115. Particularly preferably, different (types or groups of) actuators 205A and 205B are provided which are assigned to the different (types or groups of) valves 115A and 115B for actuating each of said valves, respectively.

The analysis system 1 or analysis device 200 preferably comprises one or more sensors 206. In particular, sensors 206A are designed or intended to detect liquid fronts and/or flows of fluid in the fluid system 103. Particularly preferably, the sensors 206A are designed to measure or detect, for example optically and/or capacitively, a liquid front and/or the presence, the speed, the mass flow rate/volume flow rate, the temperature and/or another value of a fluid in a channel and/or a cavity, in particular in a respectively assigned sensor portion 116, which is in particular formed by a planar and/or widened channel portion of the fluid system 103.

Particularly preferably, the sensor portions 116 are each oriented and/or incorporated in the fluid system 103 and/or fluid flows against or through the sensor portions 116 such that, in the operating position of the cartridge 100, fluid flows through the sensor portions 116 in the vertical direction and/or from the bottom to the top, or vice versa, in particular in order to make it possible or easier to accurately detect liquid.

Alternatively or additionally, the analysis device 200 preferably comprises (other or additional) sensors 206B for detecting the ambient temperature, internal temperature, atmospheric humidity, position, and/or alignment, for example by means of a GPS sensor, and/or the orientation and/or inclination of the analysis device 200 and/or the cartridge 100.

The analysis system 1 or analysis device 200 preferably comprises a control apparatus 207, in particular comprising an internal clock or time base for controlling the sequence of a test or assay and/or for collecting, evaluating and/or outputting or providing measured values in particular from the sensor apparatus 113, and/or from test results and/or other data or values.

The control apparatus 207 preferably controls or regulates the pump drive 202, the temperature-control apparatuses 204 and/or actuators 205, in particular taking into account or depending on the desired test and/or measured values from the sensor arrangement or sensor apparatus 113 and/or sensors 206.

The flows of fluid are controlled in particular by accordingly activating the pump or pump apparatus 112 and actuating the valves 115.

Particularly preferably, the pump drive 202 comprises a stepper motor, or a drive calibrated in another way, such that desired metering can be achieved, at least in principle, by means of appropriate activation.

Additionally or alternatively, the sensors 206A are used to detect liquid fronts or flows of fluid, in particular in cooperation with the assigned sensor portions 116, in order to achieve the desired fluidic sequence and the desired metering by accordingly controlling the pump or pump apparatus 112 and accordingly activating the valves 115.

Optionally, the analysis system 1 or analysis device 200 comprises an input apparatus 208, such as a keyboard, a touch screen or the like, and/or a display apparatus 209, such as a screen.

The analysis system 1 or analysis device 200 preferably comprises at least one interface 210, for example for controlling, for communicating and/or for outputting measured data or test results and/or for linking to other devices, such as a printer, an external power supply or the like. This may in particular be a wired or wireless interface 210.

The analysis system 1 or analysis device 200 preferably comprises a power supply 211, preferably a battery or an accumulator, which is in particular integrated and/or externally connected or connectable.

Preferably, an integrated accumulator is provided as a power supply 211 and is (re)charged by an external charging device (not shown) via a connection 211A and/or is interchangeable.

The analysis system 1 or analysis device 200 preferably comprises a housing 212, all the components and/or some or all of the apparatuses preferably being integrated in the housing 212. Particularly preferably, the cartridge 100 can be inserted or slid into the housing 212, and/or can be received by the analysis device 200, through an opening 213 which can in particular be closed, such as a slot or the like.

The analysis system 1 or analysis device 200 is preferably portable or mobile. Particularly preferably, the analysis device 200 weighs less than 25 kg or 20 kg, particularly preferably less than 15 kg or 10 kg, in particular less than 9 kg or 6 kg.

The fluidic, in particular pneumatic, coupling between the cartridge 100 and the analysis device 200 will be explained in greater detail in the following, it being possible for the following aspects to be implemented independently from the preceding aspects.

As already explained, the analysis device 200 can preferably be pneumatically linked to the cartridge 100, in particular to the sensor arrangement and/or to the pump apparatus 112.

Particularly preferably, the analysis device 200 is designed to supply the cartridge 100, in particular the sensor arrangement and/or the pump apparatus 112, with a working medium, in particular gas or air.

Preferably, the working medium can be compressed and/or pressurised in the analysis device 200 or by means of the analysis device 200.

Preferably, the analysis device 200 comprises a pressurised gas supply 214 for this purpose, in particular a pressure generator or compressor, preferably in order to compress, condense and/or pressurise the working medium.

The pressurised gas supply 214 is preferably integrated in the analysis device 200 or the housing 212 and/or can be controlled or regulated by means of the control apparatus 207.

Preferably, the pressurised gas supply 214 is electrically operated or can be operated by electrical power. In particular, the pressurised gas supply 214 can be supplied with electrical power by means of the power supply 211.

The analysis device 200 or pressurised gas supply 214 is preferably designed to compress the working medium to a pressure of more than 100 kPa, particularly preferably more than 150 kPa or 250 kPa, in particular more than 300 kPa or 350 kPa, and/or of less than 1 MPa, particularly preferably less than 900 kPa or 800 kPa, in particular less than 700 kPa and/or to feed said medium to the cartridge 100 at said pressure.

Preferably, air can be drawn in, in particular from the surroundings, as the working medium by means of the analysis device 200 or pressurised gas supply 214. In particular, the analysis device 200 or pressurised gas supply 214 is designed to use the surroundings as a reservoir for the working medium or the air. However, other solutions are also possible here, in particular those in which the analysis device 200 and/or pressurised gas supply 214 comprises a preferably closed or delimited reservoir, such as a tank or container, comprising the working medium, and/or is connected or connectable thereto.

Preferably, the analysis device 200 or pressurised gas supply 214 comprises an inlet, the working medium in particular being able to be drawn in and/or conducted in or to the pressurised gas supply 214 via the inlet.

Preferably, the analysis device 200 and/or pressurised gas supply 214 comprises a filter, the filter preferably being integrated in the inlet and/or it preferably being possible for the working medium to be filtered by means of the filter and/or it preferably being possible for particles to be separated from the working medium by means of the filter.

The filter is preferably designed as a micro filter or as a fine particulate air filter. Preferably, particles having a particle diameter of more than 10 µm, particularly preferably more than 8 µm or 9 µm, in particular more than 6 µm or 7 µm, more particularly preferably more than 4 µm or 5 µm, can be separated by means of the filter, the particle diameter preferably being the maximum or average diameter of the respective particles. This ensures that the channels or lines in the cartridge that convey the working medium do not become contaminated or clogged and/or that no undesired pressure loss occurs.

The analysis device 200 or pressurised gas supply 214 preferably comprises a connection element 214A, in particular in order to pneumatically connect the analysis device 200 and/or pressurised gas supply 214 to the cartridge 100, as will be explained in greater detail with reference to FIG. 11 and FIG. 12.

In the following, further details are given on a preferred construction of the sensor arrangement and sensor apparatus 113 with reference to FIG. 3 to FIG. 10.

Figure 3:
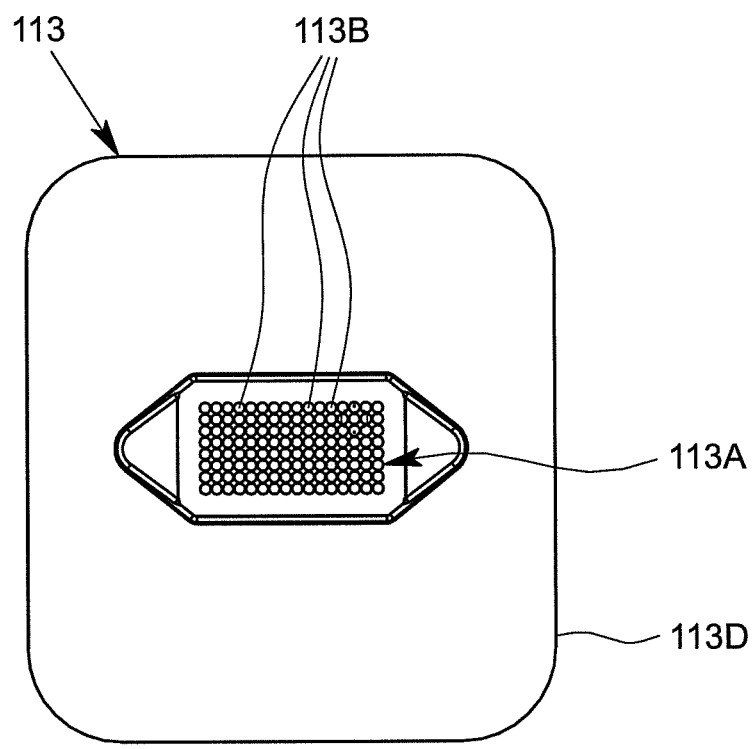
FIG. 3 is a schematic front view of a proposed sensor apparatus of the analysis system and/or cartridge.
Figure 4:
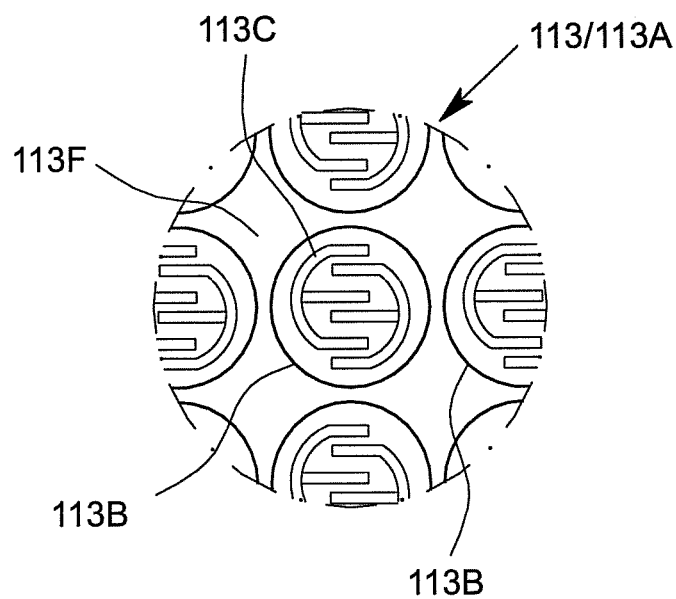
FIG. 4 is an enlarged detail from FIG. 3 illustrating a sensor field of the sensor apparatus.
Figure 5:
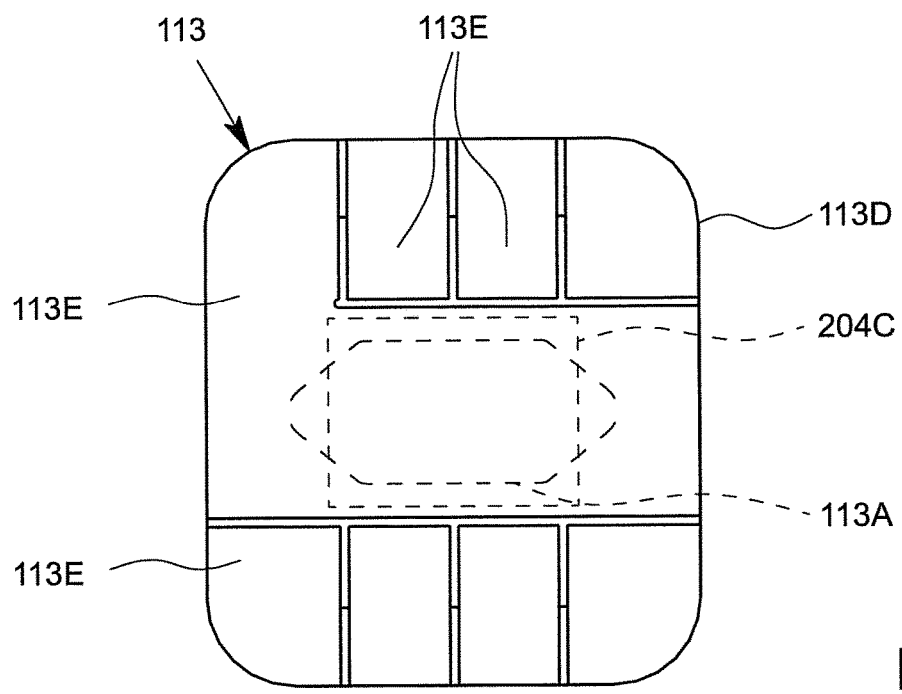
FIG. 5 is a schematic rear view of the sensor apparatus.
Figure 6:
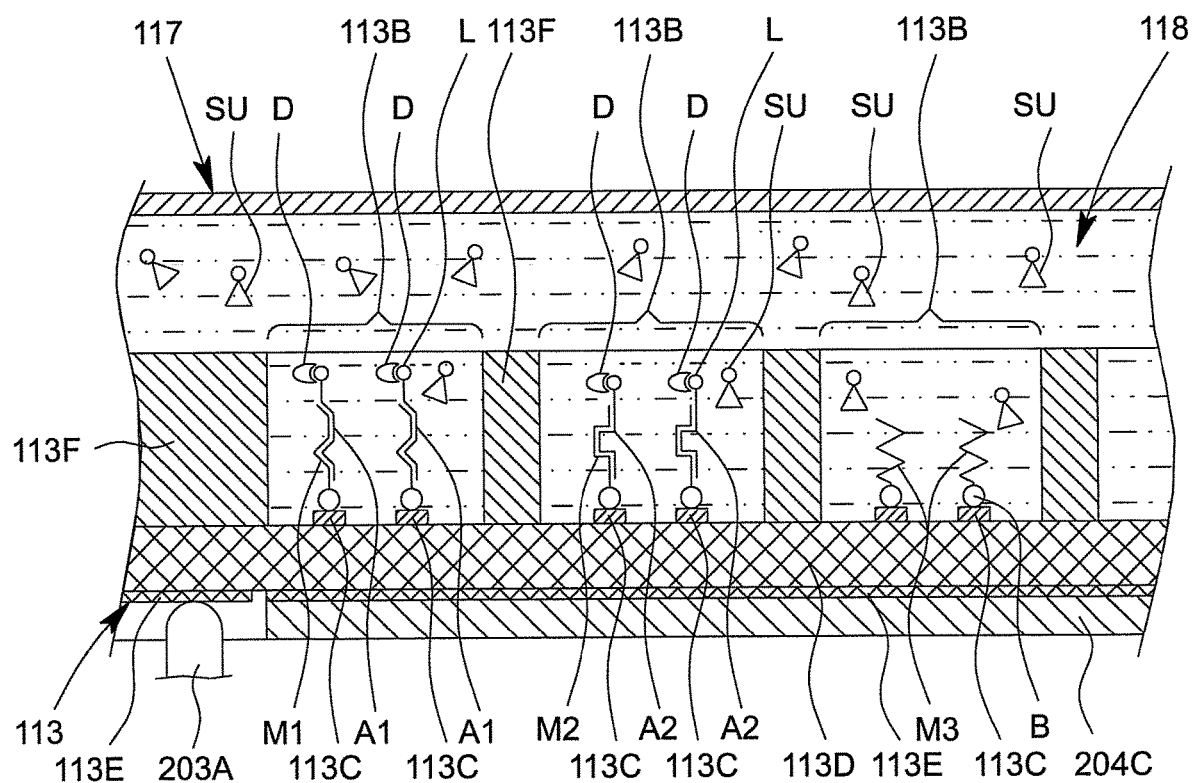
FIG. 6 is a schematic sectional view of a sensor arrangement comprising the sensor apparatus and a sensor cover that has been moved away.
Figure 7:
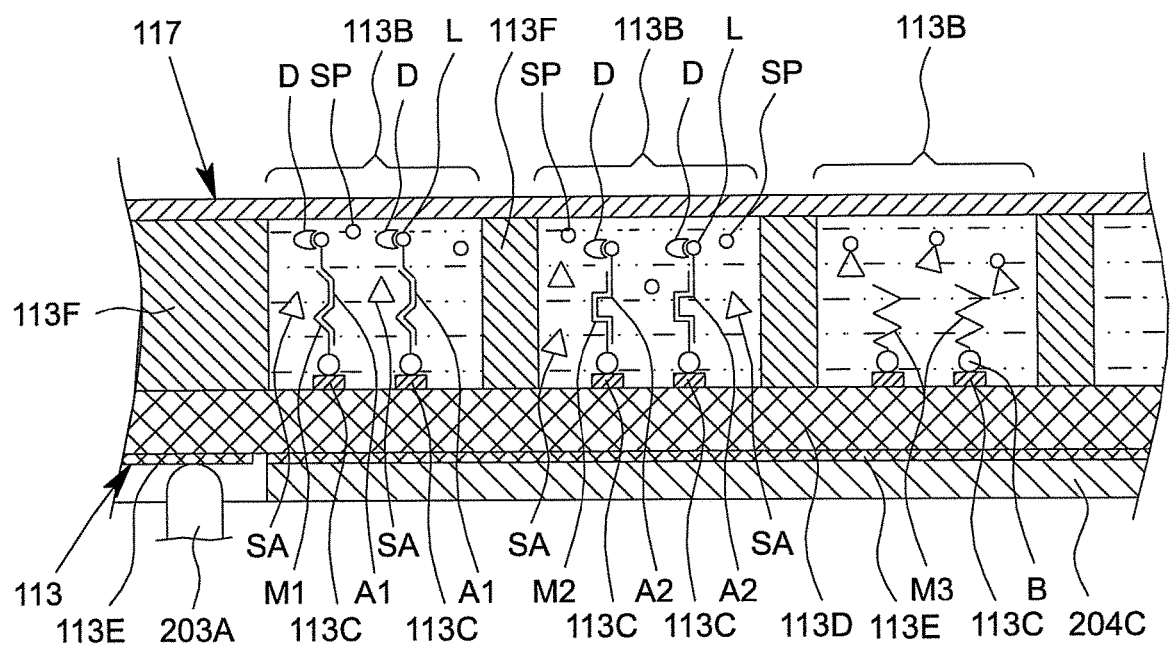
FIG. 7 is a schematic sectional view of the sensor arrangement according to FIG. 6, with the sensor cover lowered.
Figure 8:
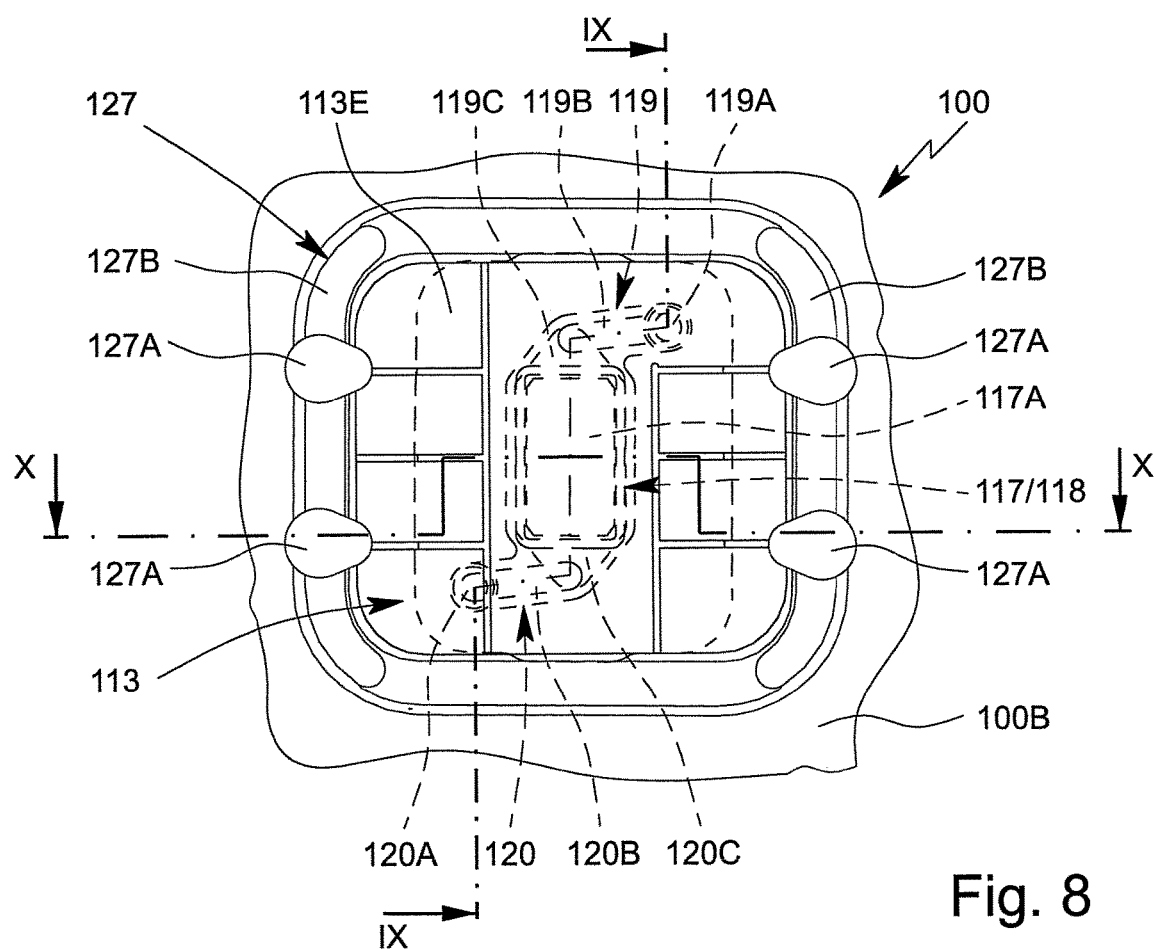
FIG. 8 is an enlarged view of the cartridge in the region of the sensor arrangement.
Figure 9:
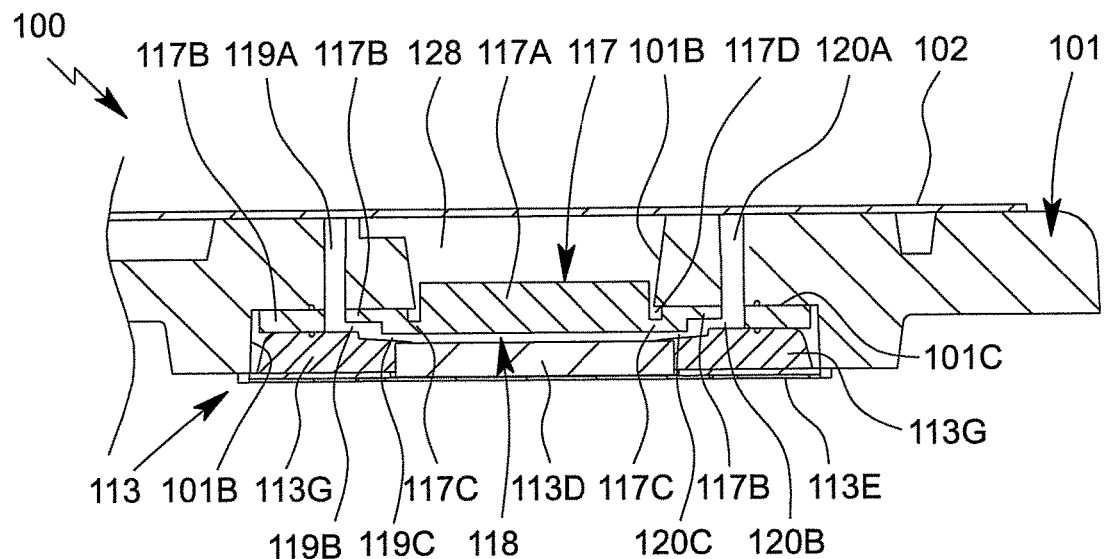
FIG. 9 is a schematic sectional view of the cartridge in the region of the sensor arrangement, along the sectional line IX-IX shown in FIG. 8.
Figure 10:
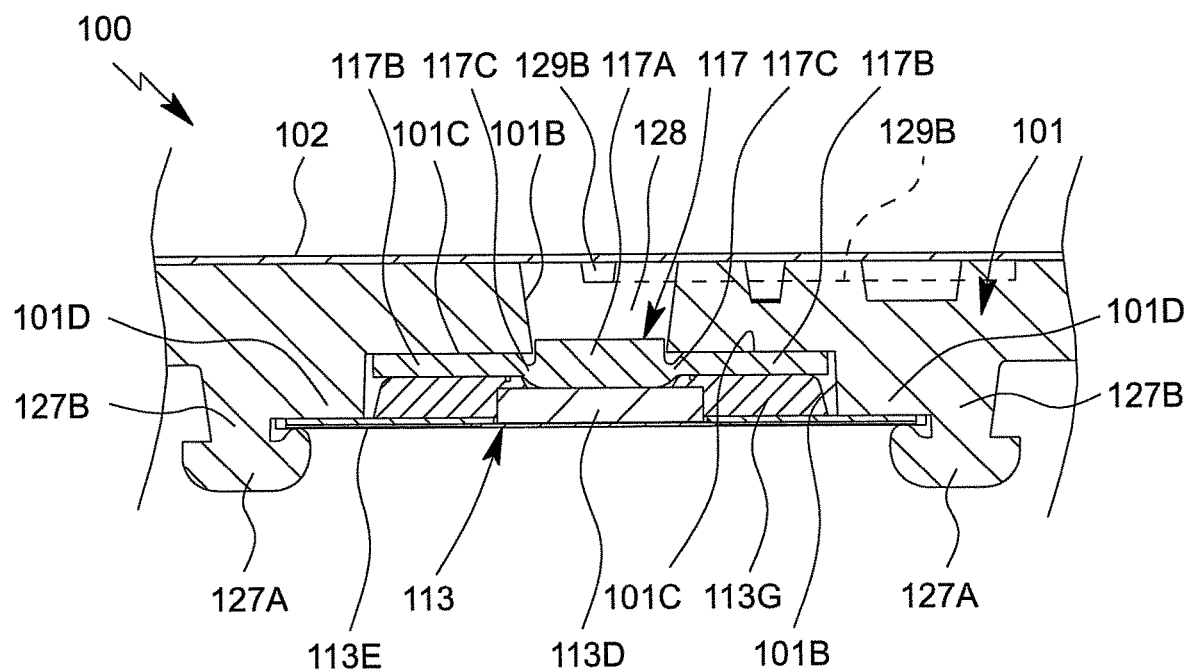
FIG. 10 is a schematic sectional view of the cartridge in the region of the sensor arrangement, along the sectional line X-X shown in FIG. 8.

FIG. 3 is a plan view of the sensor array 113A or the measuring side of the sensor apparatus 113. FIG. 4 is an enlarged detail from FIG. 3. FIG. 5 shows the connection side of the sensor arrangement or the sensor apparatus 113. FIG. 6 and FIG. 7 are each schematic sections through the sensor arrangement. FIG. 8 is an enlarged detail of the back 100B of the cartridge 100 illustrating the sensor arrangement. FIG. 9 is a section through the sensor arrangement along the line IX-IX from FIG. 8. FIG. 10 is a schematic section through the sensor arrangement along the line X-X from FIG. 8.

The sensor arrangement preferably comprises the sensor apparatus 113, a sensor cover 117 for the sensor apparatus 113, a sensor compartment 118, an inlet 119 into the sensor compartment 118 and/or an outlet 120 out of the sensor compartment 118, as shown in FIGS. 6, 7, 9 and 10.

The sensor arrangement, in particular the sensor apparatus 113, is preferably designed for electrochemically measuring or detecting analytes A of the sample P.

In particular, the sensor arrangement or sensor apparatus 113 is designed to identify, to detect and/or to determine (identical or different) analytes A bonded to capture molecules M or products derived therefrom, in particular amplification products of the analyte A or different analytes A.

The sensor arrangement is preferably designed as a multiple-part module, the sensor apparatus 113 and the sensor cover 117 preferably each forming a component of the sensor arrangement or module.

Preferably, the sensor arrangement has a layered construction, the sensor apparatus 113 preferably forming a base of the sensor arrangement and the sensor cover 117 being directly connected to the sensor apparatus 113, at least at the edge, and/or resting thereon.

The sensor apparatus 113 and the sensor cover 117 define or delimit the sensor compartment 118, preferably on the flat sides. In particular, the sensor compartment 118 is formed or arranged between the sensor apparatus 113 and the sensor cover 117.

The sensor compartment 118 preferably has, in particular when the sensor cover 117 is not actuated and/or has been moved away, a volume of greater than 0.1 μl or 0.2 μl, particularly preferably greater than 0.5 μl or 1 μl, in particular greater than 2 μl, and/or less than 10 μl or 8 μl, particularly preferably less than 6 μl or 3 μl.

The sensor arrangement, in particular the sensor apparatus 113 and the sensor cover 117, is/are preferably planar and/or plate-shaped. Preferably, the surface area of a flat side of the sensor apparatus 113 and/or sensor cover 117 is less than 400 mm$^2$ or 300 mm$^2$, particularly preferably less than 250 mm$^2$ or 150 mm$^2$, in particular less than 100 mm$^2$ or 50 mm$^2$, and/or greater than 0.01 mm$^2$ or 0.25 mm$^2$, particularly preferably greater than 1 mm$^2$ or 4 mm$^2$.

The sensor apparatus 113 preferably has a front side or measuring side and a rear side or connection side, the measuring side and the connection side each preferably forming one flat side of the in particular planar and/or plate-shaped sensor apparatus 113.

The measuring side is preferably the side of the sensor apparatus 113 facing the fluid, the sample P, the analytes A and/or the sensor compartment 118.

The connection side is preferably opposite the measuring side and/or is the side of the sensor apparatus 113 that faces away from the fluid, the sample P, the analytes A and/or the sensor compartment 118.

The sensor apparatus 113 preferably comprises a sensor array 113A on the measuring side, having a plurality of sensor cavities and/or sensor fields 113B, the sensor fields 113B preferably being circular, in a plan view of the sensor array 113A and/or being arranged so as to be directly next to one another.

Preferably, the sensor arrangement or sensor apparatus 113 or the sensor array 113A comprises more than 10 or 20, particularly preferably more than 50 or 80, in particular more than 100 or 120 and/or less than 1000 or 800 sensor fields 113B.

Preferably, the sensor fields 113B are separated or spaced apart from one another, in particular by less than 100 μm or 10 μm and/or more than 10 nm or 100 nm. Particularly preferably, all the sensor fields 113B are arranged on a surface area of less than 100 mm$^2$ and/or greater than 1 mm$^2$ and/or the sensor array 113A has a surface area of less than 100 mm$^2$ and/or greater than 1 mm$^2$.

Preferably, the sensor arrangement or sensor apparatus 113 or the sensor array 113A comprises a plurality of electrodes 113C. At least two electrodes 113C are preferably arranged in each sensor field 113B. In particular, at least two electrodes 113C in each case form a sensor field 113B.

The electrodes 113C are preferably made of metal, in particular of noble metal, such as platinum or gold, and/or said electrodes are coated, in particular with thiols.

Preferably, the electrodes 113C are finger-like and/or engage in one another, as can be seen from the enlarged detail of a sensor field 113B according to FIG. 4. However, other structural solutions or arrangements are also possible.

The sensor apparatus 113 preferably comprises a support 113D, in particular a chip, the electrodes 113C preferably being arranged on the support 113D and/or being integrated in the support 113D.

The chip or support 113D preferably contains electrical circuits or an integrated circuit, to which the electrodes 113C and/or electronic contacts 113E are connected.

Preferably, the sensor apparatus 113 comprises a housing 113G that surrounds the chip or support 113D at least in part and/or in which said chip or support is integrally cast. The housing 113G and/or the chip or the support 113D preferably supports the contacts 113E, optionally by means of a connection layer or intermediate layer.

The housing 113G leaves the sensor array 113A of the chip or support 113D free on the measuring side.

The housing 113G is in particular made of an insulating and/or hard plastics material or other material.

In the example shown, the contacts 113E, optionally together with the optional intermediate layer or a very thin portion of the housing 113G, project laterally beyond the housing 113G in part. However, if required, the housing 113G can also extend as far as the edge of the contacts 113E and/or support said contacts over the entire surface thereof or completely.

The sensor apparatus 113 or the support 113D and/or the housing 113G is/are preferably resistant to bending and/or rigid.

The sensor apparatus 113 is in particular card-like and/or designed at least substantially as a planar plate part.

The sensor apparatus 113, in particular the support 113D, preferably comprises a plurality of, in this case eight, electrical contacts or contact surfaces 113E, the contacts 113E preferably being arranged on the connection side and/or forming the connection side, as shown in FIGS. 5 and 8.

Preferably, the sensor apparatus 113 can be electrically contacted on the connection side and/or by means of the contacts 113E and/or can be electrically connected to the analysis device 200. In particular, an electrical connection can be established between the cartridge 100, in particular the sensor apparatus 113, and the analysis device 200, in particular the control apparatus 207, by electrically connecting the contacts 113E to the contact elements 203A.

Preferably, the contacts 113E are arranged laterally, in the edge region and/or in a plan view or projection around the electrodes 113C and/or the sensor array 113A, and/or the contacts 113E extend as far as the edge region of the sensor apparatus 113, in particular such that the sensor apparatus 113 can be electrically contacted, preferably by means of the connection apparatus 203 or the contact elements 203A, laterally, in the edge region and/or around the sensor temperature-control apparatus 204C, which can preferably be positioned centrally or in the middle on the support 113D, as already explained.

In particular, the sensor apparatus 113 comprises barriers or partitions between each of the sensor fields 113B, which are preferably formed by an in particular hydrophobic layer 113F having corresponding recesses for the sensor fields 113B. However, other structural solutions are also possible.

As already explained, the sensor compartment 118 is preferably arranged between the sensor apparatus 113 and the sensor cover 117, the measurement side and/or the sensor array 113A of the sensor apparatus 113 preferably defining or delimiting the sensor compartment 118.

Preferably, the sensor fields 113B and/or the electrodes 113C are fluidically interconnected by the sensor compartment 118, in particular such that the sensor fields 113B and/or electrodes 113C can come into contact with a fluid, the sample P and/or the analytes A via the sensor compartment 118.

The sensor cover 117 can preferably be moved relative to the sensor apparatus 113. In particular, the sensor cover 117 can be lowered onto the sensor apparatus 113, in particular the sensor array 113A and/or the layer 113F, preferably such that the sensor fields 113B are closed and/or fluidically separated from one another.

In particular, the fluid in the sensor compartment 118 can be displaced onto the sensor apparatus 113 by means of the sensor cover 117, and/or by lowering the sensor cover 117.

The sensor cover 117 is therefore designed to seal and/or fluidically separate the individual sensor fields 113B from one another for the actual measurement, preferably such that fluid cannot be exchanged between the sensor fields 113B.

FIG. 6 is a schematic section through the sensor arrangement with the sensor cover 117 moved away. FIG. 7 is a schematic section through the sensor arrangement with the sensor cover 117 lowered onto the layer 113F. The construction and the mode of operation of the sensor cover 117 are explained in greater detail in the following, with reference to FIG. 8 to FIG. 10.

At least when the sensor cover 117 is moved away, the sensor apparatus 113 and/or the sensor compartment 118 is fluidically linked to the fluid system 103, preferably by the inlet 119 and the outlet 120, in particular such that fluids, in particular the (pretreated) sample P or the analytes A and/or reagents, can be admitted to the measurement side of the sensor apparatus 113 or sensor array 113A.

The sensor compartment 118 can thus be loaded with fluids and/or said fluids can flow therethrough, at least when the sensor cover 117 is raised or moved away from the sensor apparatus 113 and/or the sensor array 113A.

The sensor apparatus 113 preferably comprises a plurality of in particular different capture molecules M for bonding the analytes A, different capture molecules M preferably being arranged and/or immobilised in or on different sensor fields 113B and/or being assigned to different sensor fields 113B.

The capture molecules M are in particular oligonucleotide probes.

Preferably, the capture molecules M are immobilised on the sensor apparatus 113 or the sensor array 113A or electrodes 113C by a bond and/or what is known as a spacer, in particular a C6 spacer. The formation of structures that disrupt hybridisation, e.g. hairpin structures, can be prevented by the preferred bonding of the capture molecules M by the bond B.

Particularly preferably, the electrodes 113C are provided with the capture molecules M, in this case via bonds B, in particular thiol bonds, in particular in order to bond and/or detect or identify suitable analytes A.

Different capture molecules M1 to M3 are preferably provided for the different sensor fields 113B and/or the different electrode pairs and/or electrodes 113C, in order to specifically bond different analytes A, in FIGS. 6 and 7 the analytes A1 to A3, in the sensor fields 113B.

Particularly preferably, the sensor apparatus 113 or sensor array 113A allows the analytes A bonded in each sensor field 113B to be qualitatively or quantitatively determined.

Optionally, the sensor apparatus 113 comprises capture molecules M having different hybridisation temperatures, preferably in order to bond the analytes A to the corresponding capture molecules M at different hybridisation temperatures.

The hybridisation temperature is preferably the (average) temperature at which an (amplified) analyte A or an amplification product is bonded to a corresponding capture molecule M and/or is hybridised to a corresponding capture molecule M.

The optimal hybridisation temperature is preferably the temperature at which the number of analytes A or amplification products bonded to corresponding capture molecules M is maximised and/or the number of analytes A or amplification products bonded to one another is minimised.

Preferably, the (optimal) hybridisation temperature varies for different analytes A or amplification products.

In particular, in order to achieve hybridisation at the different hybridisation temperatures, the temperature of the sensor apparatus 113, in particular of the electrodes 113C, the support 113D, the sensor compartment 118 and/or the cover 117, can be controlled or set, at least indirectly, preferably by means of the analysis device 200, in particular the temperature-control apparatus 204B and/or 204C, as already explained.

Preferably, the sensor temperature-control apparatus 204C is used to temperature-control the sensor compartment 118, in this case by being in contact with the connection side, in particular such that the desired or required or optimal hybridisation temperature is reached or set on the measuring side and/or in the sensor compartment 118.

Preferably, in the operating state, the sensor temperature-control apparatus 204C rests on the support 113D in a planar manner and/or centrally and/or so as to be opposite the sensor array 113A and/or rests on one or more contacts 113E at least in part. This makes it possible to particularly rapidly and efficiently temperature-control the sensor compartment 118 and/or the capture molecules M and analytes A.

The sensor apparatus 113, in particular the chip or support 113D, preferably comprises at least one, preferably a plurality of, electronic or integrated circuits, the circuits in particular being designed to detect electrical currents or voltages that are preferably generated at the sensor fields 113B in accordance with the redox cycling principle.

Particularly preferably, the measurement signals from the different sensor fields 113B are separately collected and/or measured by the sensor apparatus 113 and/or the circuits.

Particularly preferably, the sensor apparatus 113 or the integrated circuits directly convert the measurement signals into digital signals or data, which can in particular be read out by the analysis device 200.

Particularly preferably, the sensor apparatus 113, the chip and/or the support 113D is constructed as described in EP 1 636 599 B1.

The construction and the mode of operation of the sensor cover 117 according to a preferred embodiment are explained in greater detail in the following, with reference to FIG. 8 to FIG. 10.

FIG. 8 shows the back 100B of the cartridge 100 in the region of the sensor arrangement, the sensor cover 117 being indicated by dashed lines. FIG. 9 is a schematic sectional view of the cartridge 100 in the region of the sensor arrangement, along the sectional line IX-IX according to FIG. 8, in which the sensor cover 117 is not lowered. FIG. 10 is a schematic sectional view of the cartridge 10Q along the sectional line X-X according to FIG. 8, in which the sensor cover 117 is lowered.

The cartridge 100, in particular the main body 101, preferably comprises a depression or receptacle 101B for the sensor arrangement, sensor apparatus 113 and/or the sensor cover 117, as shown in particular in FIG. 9 and FIG. 10. In the embodiment shown, the receptacle 101 extends from the back 100B to the front 100A of the cartridge 100. In particular, the receptacle 101B is formed by an opening in the cartridge 100 and/or the main body 101. However, other solutions are also possible here.

The sensor cover 117 and/or the sensor apparatus 113 is/are inserted or installed or introduced into the depression or receptacle 101B in the main body 101, the sensor apparatus 113 preferably closing the receptacle 101B to the outside or on the back 100B of the cartridge 100.

Preferably, the sensor apparatus 113 and/or the sensor cover 117 is/are held in the receptacle 101B in a form-fit or interlocking manner, in particular in the edge region.

Preferably, the cartridge 100 and/or the main body 101 comprises a mount 127, the sensor apparatus 113 and/or the sensor cover 117 preferably being held in the receptacle 101B in a form-fit manner and/or being prevented from falling out by means of the mount 127.

In the embodiment shown, the mount 127 comprises a plurality of, in this case four, projections 127A or the mount 127 is formed by a plurality of projections 127A, the projections 127A preferably being deformed, in particular by heat staking, and/or holding the sensor apparatus 113 and/or the sensor cover 117 in the receptacle 101B in a form-fit manner. However, other solutions are also possible here, for example in which the projections 127A are formed as detents or locking pins or the like.

Preferably, the mount 127 further comprises retaining elements 127B, in this case two retaining elements 127B which are opposite to each other and are integrally formed on the mount 127. The retaining elements 127B retain the sensor apparatus 113 and/or the sensor cover 117 in the desired position and/or delimit the receptacle 101B.

The sensor cover 117 is preferably formed in one piece or forms a unit and/or membrane. In particular, the sensor cover 117 is made of and/or injection-moulded from plastics material, in particular an elastomer, for example silicone.

Preferably, the sensor cover 117 is flexible and/or extensible and/or elastically deformable at least in part, in particular in order to lower the sensor cover 117 onto the sensor apparatus 113.

The sensor cover 117 is preferably designed as a planar unit, the main plane of extension of the sensor cover 117 preferably extending, in the installed state, at least substantially in parallel with the main plane of extension of the sensor apparatus 113 and/or of the main body 101.

The sensor cover 117 preferably comprises a cover part 117A, a side part 117B and/or a connecting part 117C, the cover part 117A preferably being held and/or connected to the side part 117E by means of the connecting part 117C.

The side part 117B and/or the connecting part 117C preferably surrounds the cover part 117A laterally, peripherally, in a frame-like manner and/or in a collar-like manner. In particular, the cover part 117A is arranged centrally and the side part 117B is arranged at the edge.

The sensor cover 117 and/or the side part 117B thereof is preferably supported, mounted and/or rests on a stop or bearing 101C, and/or is held in or on the receptacle 101B. Particularly preferably, the bearing 101C is formed by the main body 101.

Preferably, the bearing 101C is designed in the manner of a shoulder or arm and/or forms a base in a rear depression in the main body 101, the base preferably comprising a central recess for forming the pressure chamber 128 that adjoins the sensor cover 117 towards the front 100A.

Preferably, the receptacle 101B in the main body 101 forms the above-mentioned bearing 101C and/or the wall for the pressure chamber 128.

The cartridge 100, the main body 101 and/or the sensor arrangement and/or sensor apparatus 113 preferably further comprises a stop 101D which is in particular peripheral or on opposite sides for supporting or mounting the sensor apparatus 113, as shown schematically in FIG. 10. In the example shown, the stop 101D engages in particular laterally overhanging regions of the contacts 113E of the sensor apparatus 113 from below. Alternatively or additionally, however, the stop 101D can for example also support the sensor apparatus 113 on the housing 113G, for example by means of a corresponding shoulder and a corresponding opening in the side part 117B of the sensor cover 117.

The cover part 117A is preferably designed to cover the sensor apparatus 113, in particular the sensor array 113A.

Particularly preferably, the cover part 117A is designed to completely cover all the sensor fields 113B and/or all of the sensor array 113A. In particular, the cover part 117A comprises a covering surface that is larger than the surface area of the sensor array 113A, in particular such that the entire sensor array 113A and/or all the sensor fields 113E can be covered and/or closed by means of the cover part 117A.

Preferably, the cover part 117A can be moved relative to the sensor apparatus 113, in particular relative to the sensor array 113A, in particular in order to close and/or fluidically separate the sensor fields 113B from one another and/or to displace the fluid in the sensor compartment 118 and/or between the cover part 117A and the layer 113F, as already explained at the outset.

The cover part 117A can preferably be lowered onto the sensor apparatus 113 in a planar manner and/or so as to have a flat side facing the sensor apparatus 113.

Preferably, the cover part 117A is at least substantially planar, flat and/or straight also in the lowered state. In particular, the cover part 117A can be lowered evenly and/or such that the cover part 117A does not curve or bend or at least substantially does not curve or bend.

In particular, in order to achieve and/or ensure an even or smooth lowering of the sensor cover 117 and/or the cover part 117A, the sensor cover 117 is preferably centrally reinforced, in particular stiffened, thickened and/or has a raised portion. This achieves and/or allows planar and/or simultaneous covering of all the sensor fields 113B, in particular the sensor fields 113B in the edge region of the sensor array 113A.

In particular, the cover part 117A is thicker and/or more rigid than the connecting part 117C and/or the side part 117B. Preferably, the thickness or material thickness of the cover part 117A is at least 1.5 times or twice the material thickness or thickness of the connecting part 117C and/or side part 117B. Preferably, the cover part 117A has a thickness or material thickness of more than 10 μm or 50 μm, particularly preferably more than 100 μm or 200 μm and/or less than 1000 μm or 500 μm.

In the example shown, the side part 117B is preferably thinner than the cover part 117A.

The connecting part 117C is preferably thinner than the side part 117B. In particular, a depression or groove 117D is formed on the side remote from the sensor compartment 118, as shown schematically in FIGS. 9 and 10. This depression or groove 117D is preferably formed peripherally around the (central) cover part 117A, such that the connecting part 117C can be very flexibly, in particular elastically, deformed in order to allow the desired placement of the cover part 117A on the sensor apparatus 113, the sensor array 113A thereof and/or the layer 113F thereof when the sensor cover 117 is actuated and/or lowered.

Preferably, the sensor cover 117 and/or the connecting part 117C has a sufficiently high restoring force to allow, if required, a return movement of the sensor cover 117 and/or the cover part 117A into the unactuated initial position shown in FIG. 9, in which position the cover part 117A is moved away from the sensor apparatus 113 and/or the sensor array 113A.

In the embodiment shown, in the unactuated state the sensor cover 117 is at least substantially planar or flat on the side facing the sensor apparatus 113 and is raised or has a raised portion in the centre, at least compared with the side part 117B and/or connecting part 117C, on the side remote from the sensor apparatus 113. Particularly preferably, the flat sides of the cover part 117A, side part 117B and/or connecting part 117C, and/or the sides thereof facing the sensor apparatus 113, lie in or form a common plane at least when the sensor cover 117 is in the initial position unactuated and/or moved away. However, other solutions are also possible, in which the cover part 117A is reinforced in another manner, for example by means of a core and/or a coating (not shown).

Preferably, the sensor cover 117 and/or the side part 117B is held and/or clamped in the edge region in a stationary manner, in particular between the sensor apparatus 113 or the housing thereof 113G on one side, and the main body 101 or the bearing 101C on the other side, in particular such that the cover part 117A is moved and/or lowered relative to the (stationary) side part 117B when the sensor cover 117 is actuated.

Preferably, the connecting part 117C is considerably thinner than the side part 117B and/or is flexible and/or extensible and/or elastically deformable at least in part, in particular such that the connecting part 117C allows a relative movement between the cover part 117A and the side part 117B.

The sensor cover 117, in particular the side part 117B, preferably seals the sensor apparatus 113 and/or the sensor compartment 118 laterally and/or at the edge.

In particular, the sensor apparatus 113 and/or the housing 113G thereof is sealingly mounted on the sensor cover 117 and/or on the side part 117B in the edge region, preferably such that no fluid can escape from the cartridge 100 and/or the receptacle 101B, in particular also when the sensor cover 117 is moved away from the sensor apparatus 113.

In the normal operating position of the cartridge 100, fluid can flow through the sensor arrangement and/or the sensor compartment 118 at least substantially vertically and/or from the top to the bottom, or vice versa. In particular, in the normal operating position of the cartridge 100, the preferably elongate sensor compartment 118 has a vertical longitudinal extension, as shown in particular in FIG. 8.

Preferably, fluid can flow through the sensor compartment 118 by means of the inlet 119 and the outlet 120. In particular, a fluid can flow into the sensor compartment 118 via the inlet 119 and can flow out of the sensor compartment 118 via the outlet 120; however, the flow direction can also be reversed. In particular, the inlet 119 can be designed or used as the outlet, at least temporarily, and the outlet 120 can be designed or used as the inlet, at least temporarily.

The inlet 119 and/or the outlet 120 is/are preferably formed by cut-outs, holes, openings, channels or the like in the main body 101, the sensor cover 117 and/or the sensor apparatus 113.

The inlet 119 and/or outlet 120 preferably comprises a plurality of portions. In the embodiment shown, the inlet 119 and/or outlet 120 comprise a first portion 119A and/or 120A, respectively, a second portion 119B or 120B, respectively, and a third portion 119C or 120C, respectively.

Preferably, the first portion 119A or 120A extends at least substantially in the main body 101 and/or orthogonally to the main plane of extension of the cartridge 100, and/or from the front 100A to the back 100B, in particular in order to transport the fluid and/or the sample P from the front 100A to the back 100B and/or to the sensor cover 117 or the side part 117B or vice versa.

Preferably, the second portions 119B or 120B, respectively, are connected to the first portions 119A or 120A, respectively.

The second portion 119B or 120B preferably extends at least substantially in parallel with the main plane of extension of the main body 101 and/or obliquely, transversely or at least substantially perpendicularly to the longitudinal extension of the sensor compartment 118 and/or the main flow direction in the sensor compartment 118, as shown in particular in FIG. 8.

Preferably, the third portions 119C or 120C, respectively, are connected to the second portions 119B or 120B, respectively, the third portions 119C or 120C, respectively, preferably directly adjoining and/or opening into the sensor compartment 118.

Preferably, the third portion 119C or 120C extends at least substantially in parallel with the main plane of extension of the cartridge 100 and/or of the main body 101 and/or substantially between the sensor cover 117 or the side part 117B on one side and the sensor apparatus 113 or the housing 113G on the other side.

Preferably, the inlet 119, in particular the third portion 119C, and/or the outlet 120, in particular the third portion 120C, is/are elongate and/or slot-like in cross section, and/or the inlet 119, in particular the third portion 119C, and/or the outlet 120, in particular the third portion 120C, diverges/diverge towards the sensor compartment 118, in particular in order to conduct the fluid and/or the sample P evenly into the sensor compartment 118.

Preferably, the inlet 119, in particular the second portion 119B, and/or the outlet 120, in particular the second portion 120B, extends/extend through the sensor cover 117, in particular the side part 117B. In particular, the sensor cover 117 forms and/or defines or delimits the inlet 119, in particular the second portion 119B, and/or the outlet 120, in particular the second portion 120B, at least in part and/or laterally. This ensures that the transition into the sensor compartment 118 and/or from the first portion 119A or 120A, respectively, to the third portion 119C or 120C, respectively, is sealed.

As already explained at the outset, the sensor cover 117, in particular the cover part 117A, can be actuated and/or lowered pneumatically and/or by means of pressurised air.

Preferably, the cartridge 100 and/or the sensor arrangement comprises the pressure chamber 128, the pressure chamber 128 preferably being delimited or defined by the main body 101, the sensor cover 117 and the cover or film 102.

Particularly preferably, the pressure chamber 128 is formed by the depression or receptacle 101B or a part thereof, and/or is sealed off from the sensor apparatus 113 by means of the sensor cover 117.

In particular, the sensor cover 117 is arranged between the pressure chamber 128 and the sensor compartment 118 and/or the sensor cover 117 separates the pressure chamber 128 from the sensor compartment 118.

Preferably, the sensor cover 117, in particular the cover part 117A, projects into the pressure chamber 128 at least in part, at least in the unactuated state of the sensor cover 117, as shown in particular in FIG. 9 and FIG. 10.

Preferably, the sensor cover 117 can be actuated and/or lowered by supplying the working medium, in particular air, to the cartridge 100, in particular the pressure chamber 128. Particularly preferably, the sensor cover 117 is actuated and/or lowered at a pressure in the pressure chamber 128 of more than 100 kPa, particularly preferably more than 150 kPa or 250 kPa, in particular more than 300 kPa or 350 kPa, and/or of less than 1 MPa, particularly preferably less than 900 kPa or 800 kPa, in particular less than 700 kPa.

Figure 11:
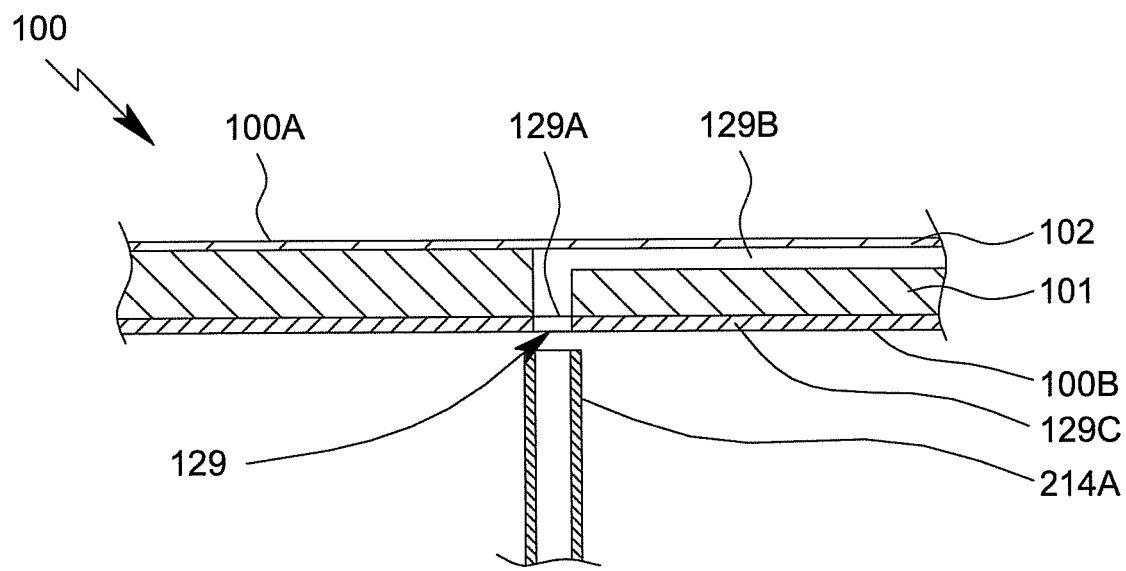
FIG. 11 is a schematic sectional view of the cartridge in the region of a pneumatic connection comprising a connection element that has been moved away.
Figure 12:
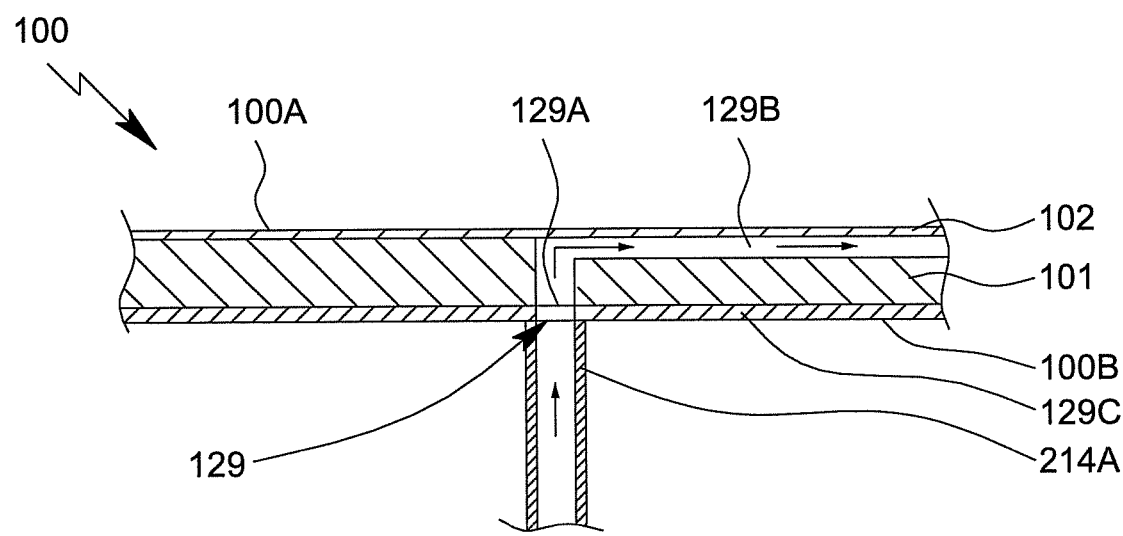
FIG. 12 is a schematic sectional view of the cartridge according to FIG. 11, with the connection element connected.

The cartridge 100 preferably comprises a pneumatic connection 129, the cartridge 100, in particular the pressure chamber 128, preferably being able to be supplied with the working medium by means of the connection 129, as shown in FIGS. 2, 11 and 12.

As shown in particular in FIG. 11 and FIG. 12, the connection 129 preferably comprises a connection opening 129A and a connection channel 129B, the connection opening 129A preferably being arranged on the back 100B of the cartridge 100 and/or being integrated in the surface of the main body 101. However, other solutions are also possible here.

Preferably, the connection channel 129B connects the connection opening 129A fluidically, in particular pneumatically, to the pressure chamber 128, as shown by the dashed lines in FIG. 10.

As already explained, the analysis device 200 can preferably be pneumatically connected to the cartridge 100, in particular the sensor arrangement, in particular by means of the connection 129, preferably in order to actuate the sensor cover 117.

In particular, the connection element 214A of the pressurised gas supply 214 can be fluidically, in particular pneumatically, connected or coupled to the connection 129.

FIG. 11 is a schematic section through the cartridge 100 in the region of the connection 129, together with the connection element 214A of which a detail is shown and which is moved away and/or not connected. FIG. 12 is a schematic section through the cartridge 100 in the region of the connection 129, together with the connection element 214A in the pressed against and/or coupled state.

Particularly preferably, the analysis device 200, in particular the pressurised gas supply 214 and/or the connection element 214A, can be positioned against the cartridge 100 and/or the connection 129 and/or coupled to the cartridge 100 and/or the connection 129 in a sealing manner, in particular in order to supply the working medium to the pressure chamber 128 and/or to actuate and/or lower the sensor cover 117.

Preferably, the cartridge 100, in particular the connection 129, and/or the connection element 214A comprises a seal 129C, the seal 129C preferably being able to establish a preferably sealed connection between the analysis device 200, in particular the pressurised gas supply 214, and the cartridge 100, in particular the pressure chamber 128.

In particular, the pressurised gas supply 214 and/or the connection element 214A can be sealingly connected to the cartridge 100 and/or the connection 129 by means of the seal 129C, in particular such that the working medium can be fed from the analysis device 200 to the cartridge 100 and/or to the pressure chamber 128.

The seal 129C is preferably arranged in the region of the connection opening 129A and/or is formed around the connection opening 129A.

In the embodiment shown, the seal 129C is preferably planar and/or is formed as a film, layer or cover. Particularly preferably, the seal 129C has a sealing surface area of more than 1 mm$^2$ or 4 mm$^2$, in particular more than 9 mm$^2$ or 25 mm$^2$, and/or less than 200 cm$^2$ or 180 cm$^2$, in particular less than 150 cm$^2$ or 120 cm$^2$.

Preferably, the seal 129C is arranged on or attached to the main body 101, in particular the back 100B of the cartridge 100, and/or is connected to the main body 101, preferably in a bonded manner, in particular by adhesion, and/or over the entire surface thereof.

In the embodiment shown, the seal 129C is assigned to the cartridge 100 and/or the cartridge 100 comprises or forms the seal 129C, preferably on the back 100B and/or on a side facing the connection element 214A. In this way, each new cartridge 100 also provides a new seal 129C and/or the cartridge 100 can be disposed of together with the seal 129C. This is conducive to hygienic testing of the sample P. However, other solutions are also possible here, in particular in which the analysis device 200, in particular the connection element 214A, comprises or forms the seal 129C, preferably on a side facing the cartridge 100.

The seal 129C is preferably made of and/or injection-moulded from foamed plastics material, in particular foamed polyethylene.

Preferably, the cartridge 100 can be moved, in particular displaced, towards the pressurised gas supply 214 and/or the connection element 214A, or vice versa, in particular in order to connect or couple the analysis device 200 to the cartridge 100 fluidically, in particular pneumatically, and/or electrically and/or thermally.

Preferably, the cartridge 100 is moved away from the connection element 214A in a first position, as shown in FIG. 11, and is positioned and/or pressed against the connection element 214A in a second position, as shown in FIG. 12.

The connection element 214A is preferably cylindrical, tubular and/or dome-like.

Particularly preferably, the connection element 214A can be pressed against the connection 129 and/or the seal 129C, preferably such that the connection element 214A and the connection 129 are interconnected or coupled together pneumatically, in particular in a gas-tight manner.

Particularly preferably, the connection element 214A, in particular the end face thereof, is positioned on the cartridge 100, in particular the connection 129 and/or the seal 129C, in the second position.

Preferably, the connection element 214A can be positioned so as to be at least substantially coaxial with the connection 129 and/or the connection opening 129A thereof.

Preferably, the internal cross-sectional area and/or external cross-sectional area of the connection element 214A is greater than the internal cross-sectional area of the connection 129 and/or the cross-sectional area of the connection opening 129A.

In particular, the end face of the connection element 214A can be connected to the cartridge 100 and/or the seal 129C in a region around the connection 129 and/or the connection opening 129A. However, other structural solutions are also possible in which the connection 129 can be plugged into the connection element 214A. In particular, other structural solutions are also possible in which the connection element 214A is designed as a hollow needle and/or can be plugged into the connection 129 and/or the connection opening 129A at least in part.

Optionally, the connection element 214A and/or the connection 129 and/or the connection opening 129A is/are conical, preferably such that the connection element 214A and/or the connection 129 centre one another (not shown). In this way, any manufacturing tolerances can be compensated.

In another embodiment (not shown), preferably prior to the first use of the cartridge 100, the connection 129 and/or the connection opening 129A is closed or sealed, and/or the cartridge 100 comprises a sealing means, such as a film, the sealing means and/or the seal 129C preferably covering and/or sealing the connection 129 and/or the connection opening 129A.

In an embodiment of this kind, in particular for a first use, the seal 129C and/or the sealing means can preferably be severed, pierced, broken and/or destroyed by means of the connection element 214A in order to produce a pneumatic connection between the analysis device 200 and the cartridge 10Q, and/or the connection element 214A can be pushed through the seal 129C and/or the sealing means and into the connection 129 and/or the connection opening 129A. This ensures that the cartridge 100, in particular the connection 129, is not contaminated prior to the first use.

In the following, a preferred sequence of a test or analysis using the proposed analysis system 1 and/or analysis device 200 and/or the proposed cartridge 100 and/or in accordance with the proposed method is explained in greater detail by way of example.

The analysis system 1, the cartridge 100 and/or the analysis device 200 is preferably designed to carry out the proposed method.

Within the context of the method according to the invention, a sample P having at least one analyte A on the basis of a fluid or a liquid from the human or animal body, in particular blood, saliva or urine, is usually first introduced into the receiving cavity 104 via the connection 104A, in order to detect diseases and/or pathogens, it being possible for the sample P to be pretreated, in particular filtered.

Once the sample P has been received, the receiving cavity 104 and/or the connection 104A thereof is fluidically closed, in particular in a liquid-tight and/or gas-tight manner.

Preferably, the cartridge 100 together with the sample P is then linked or corrected to the analysis device 200, in particular is inserted or slid into the analysis device 200.

The method sequence, in particular the flow and conveying of the fluids, the mixing and the like, is controlled by the analysis device 200 or the control apparatus 207, in particular by accordingly activating and actuating the pump drive 202 or the pump apparatus 112 and/or the actuators 205 or valves 115.

During the nucleic-acid assay, a desired volume of the sample P that is mixed and/or pretreated in the mixing cavity 107 is subsequently preferably fed to one or more reaction cavities 109, particularly preferably via (respectively) one of the upstream, optional intermediate cavities 106A to 106C and/or with different reagents or primers, in this case dry reagents S4 to S6, being added or dissolved.

In the reaction cavities 109, the amplification reactions or PCRs are carried out to copy/amplify the analytes A. This is carried out in particular by means of the assigned, preferably common, reaction temperature-control apparatus(es) 204A and/or preferably simultaneously for all the reaction cavities 109, i.e. in particular using the same cycles and/or temperature (curves/profiles).

During the nucleic-acid assay, a label L is in particular produced directly and/or during the amplification reaction(s) (in each case) and/or is attached to the analytes A and/or amplification products. This is in particular achieved by using corresponding, preferably biotinylated, primers. However, the label L can also be produced and/or bonded to the analytes A and/or amplification products V separately or later, optionally also only in the sensor compartment 118 and/or after hybridisation. In particular, during the protein assay, a label L is only bonded to analytes A after hybridisation of the analytes A to the capture molecules M.

The label L is used in particular for detecting bonded analytes A and/or amplification products. In particular, the label L can be detected or the label L can be identified in a detection process, as explained in greater detail in the following.

After carrying out the amplification reaction(s), corresponding fluid volumes and/or amplification products are conducted out of the reaction cavities 109 in succession to the sensor arrangement, in particular the sensor apparatus 113 and/or the sensor compartment 118, in particular via a group-specific and/or separate intermediate cavity 106E, 106F or 106G (respectively) and/or via the optional (common) intermediate temperature-control cavity 110.

After the sample P and/or the analytes A and/or amplification products are fed to the sensor apparatus 113, the analytes A and/or amplification products are hybridised to the capture molecules M, preferably by (actively) temperature-controlling, in particular heating, the sensor arrangement or sensor apparatus 113, in particular by means of the sensor temperature-control apparatus 204C.

When carrying out the protein assay, the sample P and/or the analytes A is/are preferably fed directly from the mixing cavity 107 to the sensor arrangement or sensor apparatus 113 and/or is/are guided past the intermediate cavity/cavities 106, reaction cavity/cavities 109 and/or the intermediate temperature-control cavity 110 via the bypass 114A.

Once the sample P, analytes A and/or amplification products are hybridised and/or bonded to the capture molecules M, detection follows, in particular by means of the preferably provided label L, or in another manner.

In the following, a particularly preferred variant of the detection is described in greater detail, specifically electro-chemical detection, but other types of detection, for example optical detection, capacitive detection or the like, may also be carried out.

Following the respective bondings/hybridisations, preferably an optional washing process takes place and/or additional reagents or liquids, in particular from the storage cavities 108B to 108E, are optionally fed in.

Subsequently and/or after the washing process, in accordance with a preferred variant of the method, detection of the analytes A and/or amplification products bonded to the capture molecules M takes place.

If the bonded analytes A and/or amplification products are still not marked and/or provided with a label L, in particular during the protein assay, the labels L are then fed to the sensor arrangement or the sensor compartment 118, preferably from the storage cavity 108E, particularly preferably in the form of a liquid reagent F5. Optionally, there is then another washing process.

In order to detect the analytes A or amplification products bonded to the capture molecules M, a reagent F4 and/or detector molecules D, in particular alkaline phosphatase/streptavidin, is/are fed to the sensor apparatus 113, preferably from the storage cavity 108D.

Within the meaning of the present invention, the term "detector molecules" is preferably understood to mean molecules that bond specifically to the marker or label L of the (bonded) analytes A or amplification products and thus allow the detection thereof.

In particular, the detector molecules D may be enzyme conjugates and/or immunoconjugates, which bond specifically to the marker or label L, in particular biotin, and comprise a reporter enzyme for converting a substrate.

In the context of the present invention, the detector molecules D are preferably based on streptavidin, which has a high affinity for biotin, and/or alkaline phosphatase, which can convert non-reactive phosphate monoesters to electrochemically active molecules and phosphate.

Preferably, a detection system is used, where the label L is based on biotin and where the detector molecules D are based on streptavidin/alkaline phosphatase. However, other detector molecules D can also be used.

The reagents F4 and/or detector molecules D can bond to the bonded analytes A or amplification products, in particular to the label L of the bonded analytes A or amplification products, particularly preferably to the biotin marker, as shown in FIG. 6.

Optionally, subsequently or after the reagents F4 and/or detector molecules D have bonded to the analytes A and/or amplification products or the labels L, an (additional) washing process and/or flushing takes place, preferably by means of the fluid or reagent F3 or wash buffer, in particular in order to remove unbonded reagents F4 and/or detector molecules D from the sensor apparatus 113.

Preferably, a reagent S7 and/or S8 and/or substrate SU for the detection, in particular from the storage cavity 106D, is lastly fed to the sensor arrangement or sensor apparatus 113, preferably together with a fluid or reagent F2 (in particular a buffer), which is suitable for the substrate SU, particularly preferably for dissolving the reagent S7 and/or S8 and/or substrate SU, the fluid or reagent F2 in particular taken from the storage cavity 108B. In particular, the reagent S7 and/or S8 can form or can comprise the substrate SU.

Preferably, p-aminophenyl phosphate (pAPP) is used as the substrate SU.

The substrate SU preferably reacts on and/or with the bonded analytes A and/or amplification products and/or detector molecules D and/or allows these to be electrochemically measured.

In order to carry out the detection and/or electrochemical measurement of the bonded analytes A or amplification products and/or after adding the substrate SU, the sensor cover 117 is preferably pneumatically actuated and/or lowered onto the sensor apparatus 113, in particular in order to fluidically separate the (individual) sensor fields 113B from one another, and/or to prevent or minimise the exchange of substances between the sensor fields 113B.

Preferably, the working medium, which is in particular pressurised by the analysis device 200 and/or the pressurised gas supply 214, is supplied to the cartridge 100, in particular the pressure chamber 128, in particular such that the pressure in the pressure chamber 128 increases and/or the sensor cover 117, in particular the cover part 117A, is lowered and/or moved towards the sensor apparatus 113 and/or seals the sensor array 113A and/or the sensor fields 113B, as already explained at the outset.

By actuating and/or lowering the sensor cover 117, chemical exchange between the sensor fields 113B is prevented. Moreover, a reaction and/or detection is prevented from being assigned to an incorrect sensor field 113B, and in this way measurement inaccuracies or errors are prevented from occurring. In particular, the sensor cover 117 increases the measurement accuracy of the proposed method.

The pneumatic actuation of the sensor cover 117 makes it possible to close the sensor fields 113B particularly rapidly and reliably.

As shown in particular in FIG. 7, the substrate SU is preferably split by the bonded detector molecules D, in particular the alkaline phosphatase of the bonded detector molecules D, preferably into a first substance SA, such as p-aminophenol, which is in particular electrochemically active and/or redox active, and a second substance SP, such as phosphate.

Preferably, the first or electrochemically active substance SA is detected in the sensor apparatus 113 or in the individual sensor fields 113B by electrochemical measurement and/or redox cycling.

Particularly preferably, by means of the first substance SA, specifically a redox reaction takes place at the electrodes 113C, the first substance SA preferably discharging electrons to or receiving electrons from the electrodes 113C.

In particular, the presence of the first substance SA and/or the respective amounts in the respective sensor fields 113B is detected by the associated redox reactions. In this way, it can be determined qualitatively and in particular also quantitatively whether and how many analytes A and/or amplification products are bonded to the capture molecules M in the respective sensor fields 113B. This accordingly gives information on which analytes A are or were present in the sample P, and in particular also gives information on the quantity of said analytes.

In particular, by means of the redox reaction with the first substance SA, an electrical current or power signal is generated at the assigned electrodes 113C, the current or power signal preferably being detected by means of an assigned electronic circuit.

Depending on the current or power signal from the electrodes 113C that is generated in this way, it is determined whether and/or where hybridisation to the capture molecules M has occurred.

The measurement is preferably taken just once and/or for the entire sensor array 113A and/or for all the sensor fields 113B, in particular simultaneously or in parallel. In particular, the bonded analytes A and/or amplification products are detected, identified or determined simultaneously or in parallel in a single or common detection process.

However, in principle, it is also possible to measure a plurality of sample portions in the sensor apparatus 113 or in a plurality of sensor apparatuses 113 in succession or separately.

The test results or measurement results are in particular electrically transmitted to the analysis device 200 or the control apparatus 207 thereof, preferably by means of the electrical connection apparatus 203, and are accordingly prepared, analysed, stored, displayed and/or output, in particular by the display apparatus 209 and/or interface 210.

After the test has been carried out, the cartridge 100 is disconnected from the analysis device 200 and/or is released or ejected therefrom, and is in particular disposed of.

Individual aspects and features of the present invention and individual method steps and/or method variants may be implemented independently from one another, but also in any desired combination and/or order.

In particular, the present invention relates also to any one of the following aspects which can be realized independently or in any combination, also in combination with any aspects described above.

1. Analysis system 1, in particular cartridge 100, for testing an in particular biological sample P, the analysis system 1 comprising a main body 101 having a plurality of channels 114, and comprising a sensor arrangement for detecting an analyte A of the sample P, the sensor arrangement comprising a sensor apparatus 113 having capture molecules M and a sensor cover 117 that is flexible at least in part for covering the sensor apparatus 113, the sensor cover 117 being able to be lowered onto the sensor apparatus 113 by actuation, characterised
in that the sensor cover 117 can be actuated and/or lowered pneumatically, and/or
in that, in the unactuated state, the sensor cover 117 is at least substantially planar on a side facing the sensor apparatus 113 and is raised in the centre on a side remote from the sensor apparatus 113, and/or
in that the sensor apparatus 113 is pressed against the sensor cover 117 in the edge region, and/or is sealingly mounted on the sensor cover 117 in the edge region, and/or
in that the sensor arrangement comprises a sensor compartment 118 between the sensor apparatus 113 and the sensor cover 117, an inlet 119 into the sensor compartment 118 and an outlet 120 out of the sensor compartment 118, the inlet 119 and/or the outlet 120 extending through the sensor cover 117.

2. Analysis system according to aspect 1, characterised in that the analysis system 1 and/or the cartridge 100 comprises a preferably pneumatic connection 129, by means of which the analysis system 1 and/or the cartridge 100 and/or the sensor cover 117 can be supplied with a working medium, in particular gas, and/or can be pneumatically actuated.

3. Analysis system according to aspect 1 or 2, characterised in that the analysis system 1 and/or the cartridge 100 and/or the sensor arrangement comprises a pressure chamber 128, the pressure chamber 128 preferably being able to be supplied with the working medium by means of the connection 129, and/or the sensor cover 117 being arranged between the pressure chamber 128 and the sensor apparatus 113 and/or fluidically separating the pressure chamber 128 from the sensor compartment 118.

4. Analysis system according to any one of the preceding aspects, characterised in that the sensor cover 117 is centrally reinforced and/or formed in one piece or forms a unit and/or is made of and/or injection-moulded from plastics material, in particular an elastomer.

5. Analysis system according to any one of the preceding aspects, characterised in that the sensor cover 117 comprises a cover part 117A that can be lowered onto the sensor apparatus 113, a side part 117B and a connecting part 117C that is flexible and/or extensible at least in part, the cover part 117A preferably being connected to the side part 117B by means of the connecting part 117C.

6. Analysis system according to aspect 5, characterised in that the cover part 117A is thicker and/or more rigid than the connecting part 117C and/or side part 117B, and/or in that the connecting part 117C is thinner than the side part 117B.

7. Analysis system according to aspect 5 or 6, characterised in that the side part 117B surrounds the cover part 117A in a collar-like manner, is held and/or clamped directly between the sensor apparatus 113 and the main body 101, and/or forms a seal for the sensor apparatus 113 and/or the sensor compartment 118 and/or the pressure chamber 128.

8. Analysis system according to any one of aspects 5 to 7, characterised in that the inlet 119 and/or the outlet 120 extends/extend through the side part 117B and/or is/are formed by the side part 117B at least in part.

9. Analysis system according to any one of the preceding aspects, characterised in that the inlet 119 and/or the outlet 120 is/are elongate and/or slot-like in cross section and/or diverges/diverge towards the sensor compartment 118.

10. Analysis system according to any one of the preceding aspects, characterised in that the sensor compartment 118 is delimited by the sensor cover 117 and the sensor apparatus 113 on the flat side, and/or fluid can flow therethrough at least substantially vertically in the normal operating position of the cartridge 100.

11. Analysis system according to any one of the preceding aspects, characterised in that the sensor apparatus 113 and/or sensor cover 117 is inserted into a depression or receptacle 101B in the main body 101, the sensor apparatus 113 and/or the sensor cover 117 preferably being held in a form-fit manner in the depression or receptacle 101B, in particular by means of heat staking the main body 101.

12. Analysis system according to any one of the preceding aspects, characterised in that the sensor apparatus 113 is designed for in particular electrochemically detecting analytes A bonded to the capture molecules M and/or comprises a sensor array 113A having a plurality of sensor fields 113B, the sensor fields 113B preferably being able to be fluidically separated from one another by lowering the sensor cover 117.

13. Analysis system according to any one of the preceding aspects, characterised in that the sensor apparatus 113 can be electrically contacted on a side remote from the sensor compartment 118 and/or comprises a plurality of electrical contacts.

14. Method for testing an in particular biological sample P, analytes A of the sample P being bonded to capture molecules M of a sensor apparatus 113 and the bonded analytes A being detected by the sensor apparatus 113,
a sensor cover 117 that is flexible at least in part being lowered onto the sensor apparatus 113 for the detection, characterised
in that the sensor cover 117 is pneumatically actuated.

15. Method according to aspect 14, characterised in that the sample P is placed into a cartridge 100, and the cartridge 100 containing the sample P is received by an analysis device 200 at least in part, the analysis device 200 preferably being pneumatically and/or electrically connected to the cartridge 100, in particular to a sensor arrangement of the cartridge 100, and/or a working medium, in particular gas, being pressurised by the analysis device 200 and being fed to the cartridge 100 in order to actuate the sensor cover 117.

What is claimed is:
1. An analysis system for testing a biological sample, the analysis system comprising;

a main body having a plurality of channels, and comprising a sensor arrangement for detecting an analyte of the sample, the sensor arrangement comprising a sensor apparatus having capture molecules and a sensor cover that is flexible at least in part for covering the sensor apparatus, the sensor cover being lowerable onto or towards the sensor apparatus in an actuated state, wherein;

in an unactuated state, the sensor cover is at least substantially planar or flat on a side facing the sensor apparatus and has a raised portion in the a center on a side remote or opposite from the sensor apparatus, and the sensor cover is held at the main body, the sensor cover being held at an edge in a depression or receptacle of the main body.

2. The analysis system according to claim 1, wherein the sensor cover is lowered pneumatically.

3. The analysis system according to claim 1, wherein the sensor apparatus is pressed or sealed against the sensor cover in an edge region.

4. The analysis system according to claim 1, characterized in that a housing of the sensor apparatus is sealingly mounted on the sensor cover in an edge region, the housing surrounding a chip or support.

5. The analysis system according to claim 4, wherein the chip or support is integrally cast in the housing.

6. The analysis system according to claim 4, wherein the housing leaves a sensor array of the chip or support free on the measuring side.

7. The analysis system according to claim 4, wherein the sensor apparatus comprises a plurality of electrical contacts or contact surfaces.

8. The analysis system according to claim 1, further comprising a pneumatic connection, by means of which at least one of the analysis system and the sensor cover can be supplied with a working medium.

9. The analysis system according to claim 8, further comprising a pressure chamber.

10. The analysis system according to claim 9, wherein the pressure chamber is able to be supplied with the working medium by means of the connection.

11. The analysis system according to claim 9, wherein the sensor cover is arranged between the pressure chamber and the sensor apparatus.

12. The analysis system according to claim 9, wherein the sensor cover fluidically separates the pressure chamber from the sensor arrangement.

13. The analysis system according to claim 1, wherein the sensor cover is centrally reinforced.

14. The analysis system according to claim 1, wherein the sensor cover is made of an elastomer.

15. The analysis system according to claim 1, wherein the sensor cover comprises a cover part that can be lowered onto the sensor apparatus; a side part and a connecting part that is flexible.

16. The analysis system according to claim 15, wherein the cover part is connected to the side part by means of the connecting part.

17. The analysis system according to claim 15, wherein the cover part is thicker and/or more rigid than at least one of the connecting part and the side part.

18. Analysis system according to claim 15, wherein the connecting part is thinner than the side part.

19. The analysis system according to claim 15, wherein the side part surrounds the cover part in a collar-shaped manner.

20. The analysis system according to claim 15, wherein the side part is held directly between the sensor apparatus and the main body.

21. The analysis system according to claim 15, wherein the side part forms a seal for the sensor apparatus.

22. The analysis system according to claim 15, wherein at least one of an inlet and an outlet extend through the side part.

23. The analysis system according to claim 1, wherein the sensor arrangement comprises a sensor compartment between the sensor apparatus and the sensor cover, an inlet into the sensor compartment and an outlet out of the sensor compartment, at least one of the inlet and the outlet extending through the sensor cover.

24. The analysis system according to claim 23, wherein at least one of the inlet and the outlet is elongated in cross section.

25. The analysis system according claim 23, wherein at least one of the inlet and the outlet diverge towards the sensor compartment.

26. The analysis system according to claim 1, wherein the sensor compartment is delimited or defined by the sensor cover and the sensor apparatus on the side facing the sensor apparatus.

27. The analysis system according to claim 1, wherein fluid can flow through the sensor compartment at least substantially vertically in a normal operating position of the cartridge.

28. The analysis system according to claim 1, wherein at least one of the sensor apparatus and the sensor cover are held in the depression or receptacle by means of heat staking the main body.

29. The analysis system according to claim 1, wherein the sensor apparatus electrochemically detects analytes bonded to the capture molecules.

30. The analysis system according to claim 1, wherein the sensor apparatus comprises a sensor array having a plurality of sensor fields.

31. The analysis system according to claim 30, wherein the sensor fields are fluidically separated from one another by lowering the sensor cover.

32. The analysis system according to claim 1, wherein the sensor apparatus has electrical contacts on a side remote from the sensor compartment.

33. The analysis system according to claim 1, wherein the sensor apparatus comprises a plurality of electrical contacts.

* * * * *